(12) United States Patent
Burlet et al.

(10) Patent No.: US 9,562,018 B2
(45) Date of Patent: Feb. 7, 2017

(54) SULPHATE SALTS OF N-(3-(4-(3-(DIISOBUTYLAMINO)PROPYL) PIPERAZIN-1-YL)PROPYL)-1H-BENZO[D]IMIDAZOL-2-AMINE, PREPARATION THEREOF AND USE OF THE SAME

(71) Applicants: ALZPROTECT, Loos (FR); UNIVERSITE DE LILLE 2 DROIT ET SANTE, Lille (FR); INSERM (Institut National de la Santé et de la Recherche Médicale), Paris (FR)

(72) Inventors: Stéphane Burlet, Croix (FR); Cécilia Estrella, Lomme (FR); Mathieu Barrier, Wavrin (FR); Patricia Melnyk, Annoeullin (FR); Nicolas Sergeant, Ronchin (FR); Luc Buee, Templemars (FR); Philippe Verwaerde, Santes (FR)

(73) Assignee: Alzprotect, Loos (FR)

( * ) Notice: Subject to any disclaimer, the term of this patent is extended or adjusted under 35 U.S.C. 154(b) by 0 days.

(21) Appl. No.: 14/655,642

(22) PCT Filed: Dec. 27, 2013

(86) PCT No.: PCT/EP2013/078068
§ 371 (c)(1),
(2) Date: Jun. 25, 2015

(87) PCT Pub. No.: WO2014/102339
PCT Pub. Date: Jul. 3, 2014

(65) Prior Publication Data
US 2016/0108003 A1 Apr. 21, 2016

(30) Foreign Application Priority Data
Dec. 27, 2012 (EP) .................................... 12306690

(51) Int. Cl.
*C07D 235/30* (2006.01)
*A61K 31/496* (2006.01)

(52) U.S. Cl.
CPC .................................. *C07D 235/30* (2013.01)

(58) Field of Classification Search
None
See application file for complete search history.

(56) References Cited

FOREIGN PATENT DOCUMENTS

WO     2006/051489 A1     5/2006

OTHER PUBLICATIONS

Rittman et al. ACHR, vol. 11(6),pp. 8-10 (2012).*
Ludolph et al. Eur. J.Neurol. 16(3) pp. 297-309 (2009).*
Hong-Qi et al. Translational Neurodegenration, pp. 1-12 (2012).*
Zhang et al. Molecular Brain 2011, 4:3, pp. 1-13.*
O'Brien et al. Annu Rev Neurosci. 2011 ; 34: 185-204.*
Berge, Stephen M. et al., "Pharmaceutical Salts" Journal of Pharmaceutical Sciences (1977), vol. 66(1), pp. 1-19.
Stahl, P. Heinrich et al, "Handbook of Pharmaceutical Salts: Properties, Selection, and Use" International Union of Pure and Applied Chemistry (IUPAC), (2002), pp. 212-217 XP003024996.
The International Search Report (ISR) with Written Opinion for PCT/EP2013/078068, dated Mar. 28, 2014, pp. 1-10.

* cited by examiner

*Primary Examiner* — Emily Bernhardt
(74) *Attorney, Agent, or Firm* — McDonnell Boehnen Hulbert & Berghoff

(57) ABSTRACT

The present invention relates to sulphate salts of N-(3-(4-(3-(diisobutylamino)propyl)piperazin-1-yl)propyl)-1H-benzo[d]imidazol-2-amine and pharmaceutically acceptable solvates thereof, preparation thereof, pharmaceutical compositions containing them and use of the same in the treatment and/or prevention of neurodegenerative diseases.

7 Claims, 11 Drawing Sheets

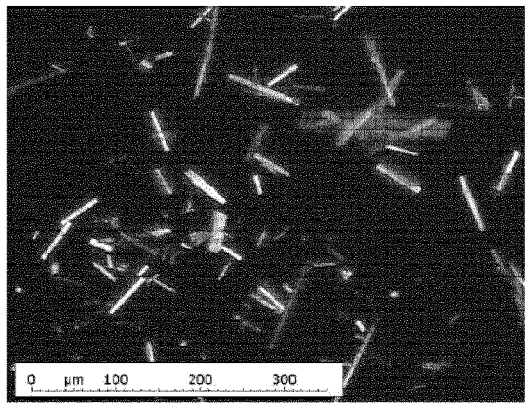 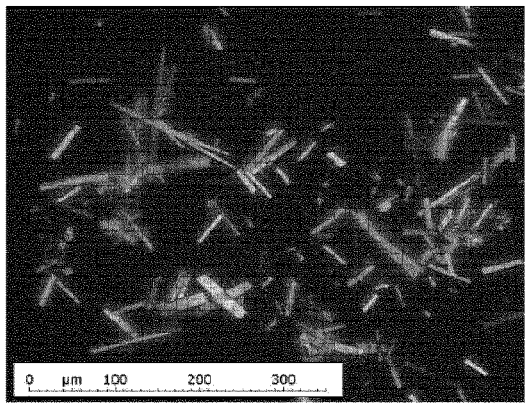
Figure 13-a                    Figure 13-b
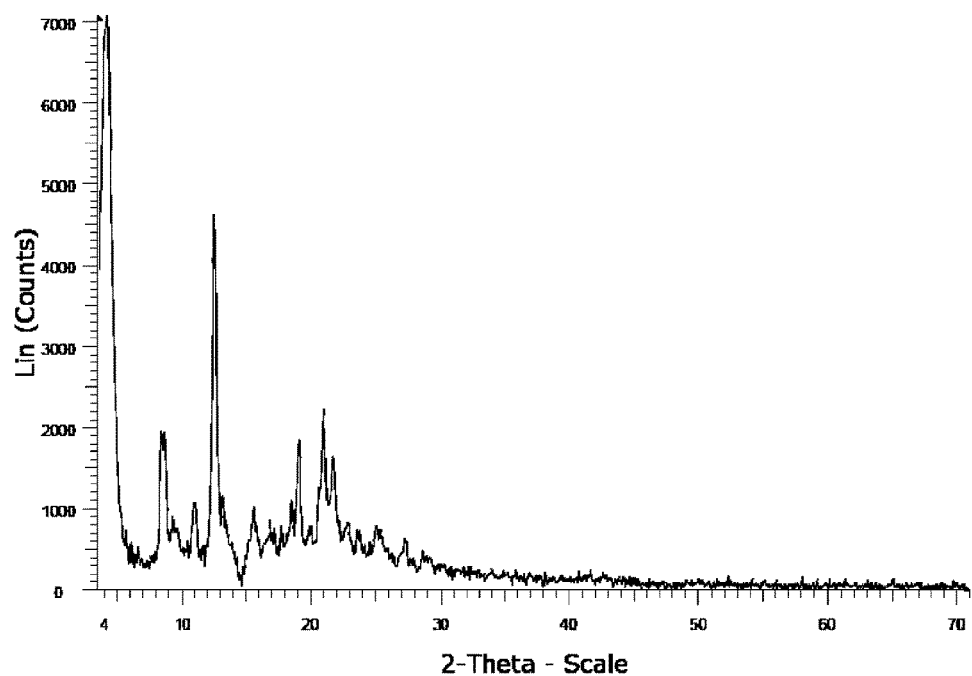
Figure 14

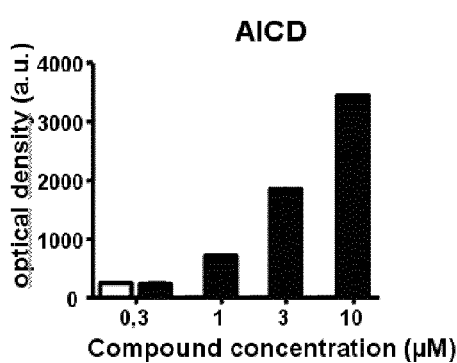
Figure 19-a
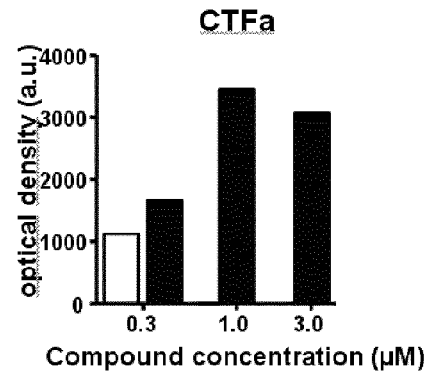
Figure 19-b
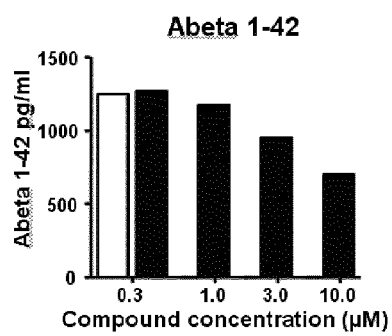
Figure 19-c
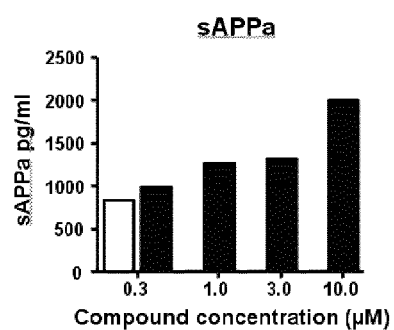
Figure 19-d
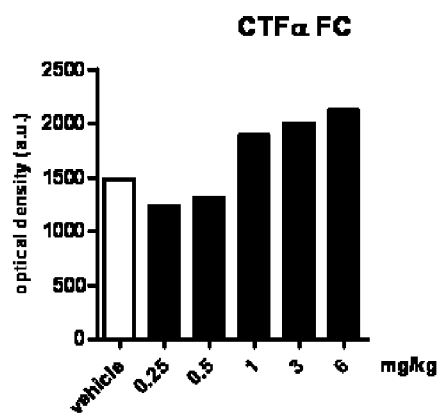
Figure 20
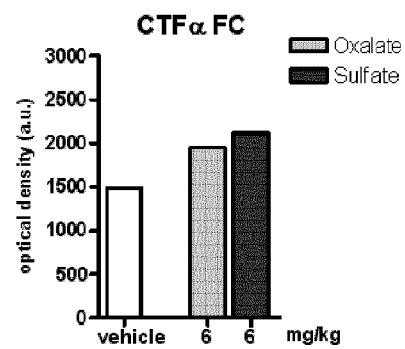
Figure 21

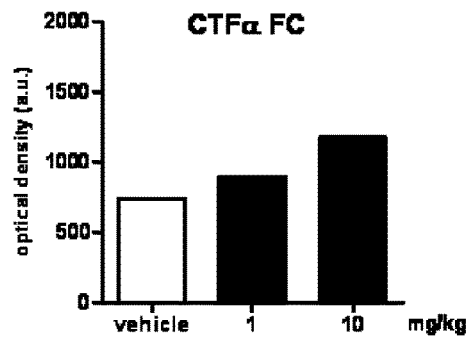
Figure 22-a
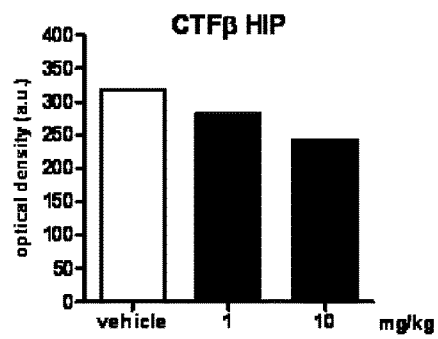
Figure 22-b
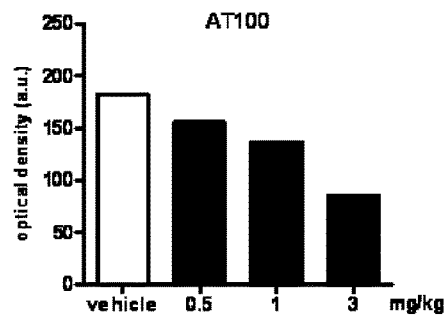
Figure 23-a
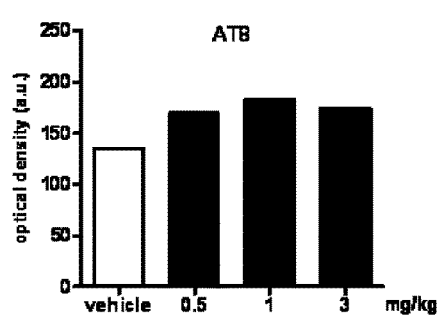
Figure 23-b
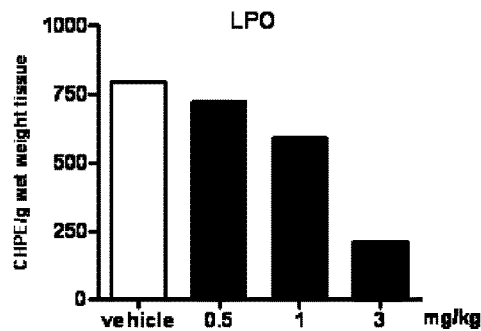
Figure 23-c

SULPHATE SALTS OF N-(3-(4-(3-(DIISOBUTYLAMINO)PROPYL) PIPERAZIN-1-YL)PROPYL)-1H-BENZO[D] IMIDAZOL-2-AMINE, PREPARATION THEREOF AND USE OF THE SAME

This application is a U.S. national phase of International Application No. PCT/EP2013/078068, filed Dec. 27, 2013, which claims priority from European Patent application no. EP 12306690, filed Dec. 27, 2012, the disclosure of each of which is hereby incorporated by reference in its entirety.

The present invention relates to novel sulphate salts of N-(3-(4-(3-(diisobutylamino)propyl)piperazin-1-yl)propyl)-1H-benzo[d]imidazol-2-amine and pharmaceutically acceptable solvates thereof, their preparation, pharmaceutical compositions containing them and use of the same in the treatment and/or prevention of neurodegenerative diseases.

BACKGROUND OF THE INVENTION

N-(3-(4-(3-(diisobutylamino)propyl)piperazin-1-yl)propyl)-1H-benzo[d]imidazol-2-amine which has the structure of Formula I Formula I

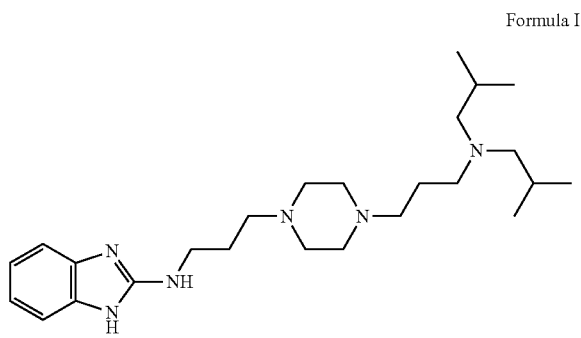 [SMILES: CC(C)CN(CCCN1CCN(CCCNc2nc3ccccc3[nH]2)CC1)CC(C)C]

belongs to a family of 1,4-bis(3-aminopropyl)piperazine derivatives previously disclosed in WO2006/051489 and which are useful for the treatment and/or prevention of neurodegenerative diseases.

The free base form of this compound presents long term stability issues likely due to oxidations occurring at the piperazine ring. In addition, the free base form does not crystallize. In terms of pharmaceutical development, crystalline forms of active ingredients are indeed preferred. They generally overcome stability issues and open up to crystallization and/or recrystallization processes which are suitable for industrial scale purification, high batch to batch reproducibility, in particular with regards to crystallinity.

Although it is known that the salification of a pharmaceutically active molecule (PAM) may improve its physicochemical properties, the selection of a suitable salt remains a complex process. Indeed, improving physico-chemical properties goes way beyond obtaining stable solid materials. These solids must comprise a crystallized phase which has a good crystallinity and a defined morphology. In other aspects, salt forms may provide other benefits such as improving water solubility but can also be equally detrimental due to hygroscopicity, stability issues or intreseque toxicity. Hence, salt selection cannot be made arbitrarily and warrants in depth studies in the first place.

The oxalate salt of N-(3-(4-(3-(diisobutylamino)propyl) piperazin-1-yl)propyl)-1H-benzo[d]imidazol-2-amine, which by the way was reported in WO2006/051489, partly overcomes the above-mentioned drawbacks encountered with the free base. However, 4 equivalents of oxalic acid are necessary to obtain the oxalate salt as a stable powder. Consequently, the percentage by weight of pharmaceutically active molecule with oxalate salts drops to as low as 54%. The amount of drug to be administered for a given dose of PAM is thus significantly increased.

Furthermore, oxalates are not considered as one of the most pharmaceutically acceptable salt anymore. Oxalate salts are in certain cases nephrotoxic, for instance naftidofuryl oxalate is known to cause calcium oxalate crystalluria and thus kidney stones in elderly patients. In addition, due to the low solubility of calcium oxalate, increased concentration of calcium oxalate in body fluids, including urine (hyperoxaluria), can lead to the deposition of calcium oxalate (oxalosis) in the kidney tissue (nephrocalcinosis) or urinary tract (urolithiasis). Oxalosis can involve many different organs when kidneys fail to clear calcium oxalate. Deposits in blood vessels can cause painful skin ulcers that do not heal, deposits in bone marrow cause anaemia and deposits in the heart cause abnormalities of heart rhythm or poor heart function. Patients suffering from neurodegenerative diseases are generally old and suffer from other pathologies for which they receive other medications. Their kidneys are thus already highly solicited for the excretion of the drugs taken by these patients who by the way are less aware of thirst sensations and thus prone to dehydration. Excess calcium oxalate is eventually excreted in patients who have healthy kidneys and who drink a lot of water. Excess calcium oxalate is indeed a real issue in therapy, especially for the elderly. In addition, treatments of neurodegenerative diseases are often chronic, over very long periods of time, if not over lifetime. Applicant considered that due to their potential kidney and urinary tract toxicity, oxalate salts would add an undue burden to patients already weakened by their condition. Applicant thus considered oxalate salts as pharmaceutically unacceptable, especially since N-(3-(4-(3-(diisobutylamino)propyl)piperazin-1-yl)propyl)-1H-benzo[d]imidazol-2-amine requires 4 equivalents of the salt counter-ion to remain stable. Therefore, even though oxalate salts allow obtaining stable solid materials, they imply risking toxic side effects.

There is thus still a need in the art for stable, crystalline and non hygroscopic salts of N-(3-(4-(3-(diisobutylamino) propyl)piperazin-1-yl)propyl)-1H-benzo[d]imidazol-2-amine that do not present the above-mentioned drawbacks in terms of salt formation and toxicity.

SUMMARY OF THE INVENTION

The present invention is based on the unexpected findings that sulphate salts of N-(3-(4-(3-(diisobutylamino)propyl) piperazin-1-yl)propyl)-1H-benzo[d]imidazol-2-amine provide stable free flowing crystalline powders which are not hygroscopic and satisfy to the demanding criteria set forth above.

The invention thus concerns a sulphate salt of N-(3-(4-(3-(diisobutylamino)propyl)piperazin-1-yl)propyl)-1H-benzo[d]imidazol-2-amine and pharmaceutically acceptable solvates thereof.

Sulphate salts of N-(3-(4-(3-(diisobutylamino)propyl)piperazin-1-yl)propyl)-1H-benzo[d]imidazol-2-amine and solvates thereof are obtained as powders which have a crystalline phase with good crystallinity and defined morphology. The sulphate salts of the invention are moreover especially suitable for the preparation of pharmaceutical compositions containing them. They are pharmaceutically acceptable and up to the Applicant's knowledge they are not associated with any intreseque toxicity of any kind. In this respect, Applicant has carried out several in vivo chronic studies with sulphate salts of N-(3-(4-(3-(diisobutylamino)propyl)piperazin-1-yl)propyl)-1H-benzo[d]imidazol-2-amine and has not observed any unexpected toxicity event to date.

Moreover, when compared to other salts, such as oxalate salts, the lower molecular weight of sulphate ions allows for an increased weight ratio of N-(3-(4-(3-(diisobutylamino)propyl)piperazin-1-yl)propyl)-1H-benzo[d]imidazol-2-amine relative to the total weight of the salt thereof. For instance, the percentage by weight of PAM with disulphate salts is of 69%. Therefore, when compared to the oxalate salt, the amount of sulphate salt required for a given dose of N-(3-(4-(3-(diisobutylamino)propyl)piperazin-1-yl)propyl)-1H-benzo[d]imidazol-2-amine is reduced. This in return decreases the amount of product administered to a patient and consequently reduces the production costs of pharmaceutical compositions containing N-(3-(4-(3-(diisobutylamino)propyl)piperazin-1-yl)propyl)-1H-benzo[d]imidazol-2-amine.

DETAILED DESCRIPTION OF THE INVENTION

The compounds of the invention are sulphate salts of N-(3-(4-(3-(diisobutylamino)propyl)piperazin-1-yl)propyl)-1H-benzo[d]imidazol-2-amine and pharmaceutically acceptable solvates thereof. More particularly, the sulphate salts of the invention and solvates thereof are those of Formula II

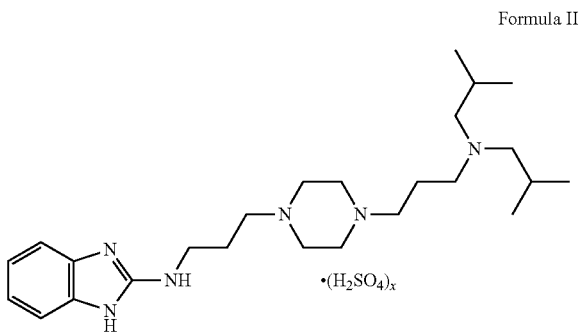 [SMILES: CC(C)CN(CCCN1CCN(CCCNc2nc3ccccc3[nH]2)CC1)CC(C)C]

Formula II wherein x is 0.5 to 4, preferably x is 0.5 to 3.5, more preferably x is 0.9 to 3.
In other words, the sulphate salt of N-(3-(4-(3-(diisobutylamino)propyl)piperazin-1-yl)propyl)-1H-benzo[d]imidazol-2-amine contains 0.5 to 4 equivalents, preferably 0.5 to 3.5 equivalents, more preferably 0.9 to 3 equivalents of sulphate for one molecule of N-(3-(4-(3-(diisobutylamino)propyl)piperazin-1-yl)propyl)-1H-benzo[d]imidazol-2-amine.

In one embodiment, x is 2.5 to 3.5, preferably 2.6 to 3.2, more preferably x is 2.8 to 3, even more preferably x is about 2.9 or x is 2.9.

In another embodiment, x is 1.5 to 2.5, preferably x is 1.5 to 2.1, more preferably x is 1.7 to 1.9, even more preferably x is about 1.8 or x is 1.8.

In yet another embodiment, x is 0.5 to 1.5, preferably x is 0.7 to 1.3, more preferably x is 0.9 to 1.1, even more preferably x is about 1 or x is 1.

In another embodiment, x is 1.7 to 2.3, preferably x is 1.9 to 2.1, more preferably x is about 2 or x is 2.

In a particular embodiment, the sulphate salt of Formula II is in the form of a pharmaceutically acceptable solvate, preferably a hydrate. The solvate stoichiometry is between 0.5 to 5, preferably between 1 to 4, more preferably between 1.5 to 2.5, still more preferably y is 1.8 to 2.2, even more preferably 2 or about 2 molecules of solvate for 1 molecule of sulphate salt of Formula II.

Preferred pharmaceutically acceptable solvates of sulphate salts of Formula II are those of Formula III

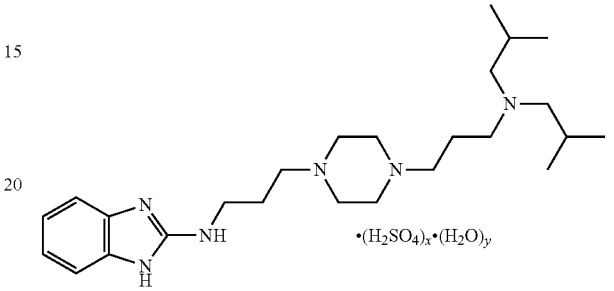

Formula III wherein
x is as defined above in Formula II, and
y is 0.5 to 5, preferably y is 1 to 4, more preferably y is 1.5 to 2.5, still more preferably y is 1.8 to 2.2, even more preferably y is about 2 or y is 2.

Preferred compounds of Formula III are those wherein, x is 0.5 to 1.5, preferably 0.8 to 1.2, more preferably x is 0.9 to 1.1, even more preferably x is about 1 or x is 1.

Particularly preferred compounds of the invention are compounds of Formula III wherein x is about 1 and y is about 2, or x is 1 and y is 2.

Applicant has shown that a sulphate salt of N-(3-(4-(3-(diisobutylamino)propyl)piperazin-1-yl)propyl)-1H-benzo[d]imidazol-2-amine and pharmaceutically acceptable solvates thereof are useful for rectifying the metabolism of the Amyloid Protein Precursor (APP) on four essential points:
1) increasing the carboxy-terminal fragments of APP (APP-CTFs) which all in common possess the last 50 amino-acids of APP, and especially those having potential physiological activities, such as the α-stubs (APP-CTF alpha) and the γ-stubs (APP-CTF gamma or AICD for APP intra cellular domain),
2) increasing the secretion of sAPP a that presents neuroprotective/neurotrophic properties,
3) decreasing the production of the neurotoxic by-products of APP, i.e. β-amyloid (Aβ) peptides, especially in their form x-42,
4) without modifying the APP expression and in absence of neurotoxicity.

The sulphate salts of the invention and solvates thereof are indeed useful in orienting APP metabolism towards non-amyloidogenic pathways in the frontal cortex and the hippocampus.

Applicant has also shown that a sulphate salt of N-(3-(4-(3-(diisobutylamino)propyl)piperazin-1-yl)propyl)-1H-benzo[d]imidazol-2-amine and pharmaceutically acceptable solvates thereof are useful for altering the pathological Tau protein phosphorylation while alleviating oxidative stress processes. Tau proteins interact with tubulin to stabilize microtubules and promote tubulin assembly into microtubules, microtubule stability being controlled by isoforms and phosphorylation. Tau pathologies comprise mechanisms leading to abnormal modifications of microtubule-associated Tau proteins, progressive aggregation and accumulation into fibrillar material inside degenerating neurons to form the so-called neurofibrillary tangles (NFT).

In addition, and contrary to other salts, their physicochemical properties are especially useful with regards to drug formulation or safety, solubility, stability, crystallinity, morphology and toxicity.

The sulphate salts of the invention are thus useful as a medicament, in particular for treating or preventing neurodegenerative diseases and all diseases wherein a dysfunction of the APP metabolism is observed, including but not limited to Alzheimer's disease, amyloid angiopathies, dementia with Lewy bodies (DLB) and Down syndrome.

The sulphate salts of the invention are thus useful as a medicament, in particular for treating or preventing neurodegenerative diseases and all diseases wherein a dysfunction of the Tau proteins phosphorylation is observed, including but not limited to tauopathies such as frontotemporal dementia with Parkinsonism linked to chromosome 17.

Hence, the invention also concerns a sulphate salt of N-(3-(4-(3-(diisobutylamino)propyl)piperazin-1-yl)propyl)-1H-benzo[d]imidazol-2-amine or a pharmaceutically acceptable solvate thereof as defined herein for use in treating and/or preventing a disease selected from neurodegenerative diseases including Alzheimer's disease, dementia with Lewy bodies (DLB), amyotrophic lateral sclerosis (ALS) with frontotemporal dementia, inclusion body myopathy with Paget's disease of bone and/or frontotemporal dementia (IBMPFD), frontotemporal lobar degeneration, synucleopathies, Huntington's disease and Parkinson's disease, amyloidopathies including amyloid angiopathies, tauopathies including frontotemporal dementia with Parkinsonism linked to chromosome 17, neuromuscular diseases with protein inclusions, as well as developmental diseases including Down syndrome. Preferably, the disease is selected from Alzheimer's disease, amyotrophic lateral sclerosis (ALS) with frontotemporal dementia, inclusion body myopathy with Paget's disease of bone and/or frontotemporal dementia (IBMPFD), frontotemporal lobar degeneration, synucleopathies, Huntington's disease, amyloidopathies including amyloid angiopathies, tauopathies including frontotemporal dementia with Parkinsonism linked to chromosome 17. More preferably, the disease is selected from Alzheimer's disease, synucleopathies, amyloidopathies including amyloid angiopathies, and tauopathies including frontotemporal dementia with Parkinsonism linked to chromosome 17. Even more preferably, the disease is selected from Alzheimer's disease and tauopathies including frontotemporal dementia with Parkinsonism linked to chromosome 17.

In other terms, the invention also provides for a method of treating and/or preventing a disease selected from neurodegenerative diseases, amyloidopathies, tauopathies and developmental diseases, in particular those cited above as well as embodiments thereof, comprising administering to a patient in need thereof a pharmaceutically effective amount of a sulphate salt of N-(3-(4-(3-(diisobutylamino)propyl)piperazin-1-yl)propyl)-1H-benzo[d]imidazol-2-amine or a pharmaceutically acceptable solvate thereof as described herein. In a particular embodiment, the disease is selected from Alzheimer's disease and tauopathies.

In one particular embodiment, the invention also concerns a sulphate salt of N-(3-(4-(3-(diisobutylamino)propyl)piperazin-1-yl)propyl)-1H-benzo[d]imidazol-2-amine or a pharmaceutically acceptable solvate thereof as defined herein for use in delaying in a patient the onset of a disease selected from neurodegenerative diseases including Alzheimer's disease, dementia with Lewy bodies (DLB), amyotrophic lateral sclerosis (ALS) with frontotemporal dementia, inclusion body myopathy with Paget's disease of bone and/or frontotemporal dementia (IBMPFD), frontotemporal lobar degeneration, synucleopathies, Huntington's disease and Parkinson's disease, amyloidopathies including amyloid angiopathies, tauopathies including frontotemporal dementia with Parkinsonism linked to chromosome 17, neuromuscular diseases with protein inclusions, as well as developmental diseases including Down syndrome. Preferably, the disease is selected from Alzheimer's disease, amyotrophic lateral sclerosis (ALS) with frontotemporal dementia, inclusion body myopathy with Paget's disease of bone and/or frontotemporal dementia (IBMPFD), frontotemporal lobar degeneration, synucleopathies, Huntington's disease, amyloidopathies including amyloid angiopathies, tauopathies including frontotemporal dementia with Parkinsonism linked to chromosome 17. More preferably, the disease is selected from Alzheimer's disease, synucleopathies, amyloidopathies including amyloid angiopathies, and tauopathies including frontotemporal dementia with Parkinsonism linked to chromosome 17. Even more preferably, the diseases are selected from Alzheimer's disease and tauopathies including frontotemporal dementia with Parkinsonism linked to chromosome 17.

In other terms, the invention provides for a method for delaying in a patient the onset of a disease selected from neurodegenerative diseases, amyloidopathies, tauopathies and developmental diseases, in particular those cited above as well as embodiments thereof, comprising administering to a patient in need thereof a pharmaceutically effective amount of a sulphate salt of the invention or a pharmaceutically acceptable solvate thereof. In a particular embodiment, the disease is selected from Alzheimer's disease and tauopathies.

According to a further feature of the present invention there is provided a method for modulating APP metabolism, in a patient, preferably a warm blooded animal, and even more preferably a human, in need of such treatment, which comprises administering to said patient an effective amount of a sulphate salt of N-(3-(4-(3-(diisobutylamino)propyl)piperazin-1-yl)propyl)-1H-benzo[d]imidazol-2-amine of the present invention, or a pharmaceutically acceptable solvate thereof.

According to still a further feature of the present invention there is provided a method for altering pathological Tau protein phosphorylation while alleviating oxidative stress processes in a patient, preferably a warm blooded animal, and even more preferably a human, in need of such treatment, which comprises administering to said patient an effective amount of sulphate salt of N-(3-(4-(3-(diisobutylamino)propyl)piperazin-1-yl)propyl)-1H-benzo[d]imidazol-2-amine of the present invention or a pharmaceutically acceptable solvate thereof.

The invention also provides pharmaceutical compositions comprising a sulphate salt of N-(3-(4-(3-(diisobutylamino)propyl)piperazin-1-yl)propyl)-1H-benzo[d]imidazol-2-amine or a pharmaceutically acceptable solvate thereof as described herein and at least one pharmaceutically acceptable carrier, diluent, excipient and/or adjuvant. In one embodiment, the invention also covers pharmaceutical compositions which contain, in addition to a sulphate salt of N-(3-(4-(3-(diisobutylamino)propyl)piperazin-1-yl)propyl)-1H-benzo[d]imidazol-2-amine or a pharmaceutically acceptable solvate thereof as active ingredient, additional therapeutic agents and/or active ingredients.

According to one embodiment, the sulphate salts of N-(3-(4-(3-(diisobutylamino)propyl)piperazin-1-yl)propyl)-1H-benzo[d]imidazol-2-amine of the invention, as well as their pharmaceutical acceptable solvates may be administered as part of a combination therapy. Thus, are included within the scope of the present invention embodiments comprising co-administration of compositions and medicaments which contain, in addition to a sulphate salt of the present invention or a pharmaceutically acceptable solvate thereof as active ingredient, additional therapeutic agents and/or active ingredients. Such multiple drug regimens, often referred to as "combination therapy", may be used in the treatment and/or prevention of any of the diseases or conditions mediated by or associated with APP metabolism modulation. The use of such combinations of therapeutic agents is especially pertinent with respect to the treatment of the above-mentioned neurodegenerative diseases within a patient in need of treatment or one at risk of becoming such a patient.

In addition to the requirement of therapeutic efficacy, which may necessitate the use of active agents in addition to the sulphate salts of N-(3-(4-(3-(diisobutylamino)propyl)piperazin-1-yl)propyl)-1H-benzo[d]imidazol-2-amine or pharmaceutically acceptable solvates thereof, there may be additional rationales which compel or highly recommend the use of combinations of drugs involving active ingredients which represent adjunct therapy, i.e., which complement and supplement the function performed by the sulphate salts of N-(3-(4-(3-(diisobutylamino)propyl)piperazin-1-yl)propyl)-1H-benzo[d]imidazol-2-amine of the present invention or pharmaceutically acceptable solvates thereof. Suitable supplementary therapeutic agents used for the purpose of auxiliary treatment include drugs which, instead of directly treating and/or preventing a disease or condition mediated by or associated with APP metabolism, treat diseases or conditions which directly result from or indirectly accompany the basic or underlying APP metabolism modulated disease or condition.

According to a further feature of the present invention, a sulphate salt of N-(3-(4-(3-(diisobutylamino)propyl)piperazin-1-yl)propyl)-1H-benzo[d]imidazol-2-amine, a pharmaceutically acceptable solvate thereof may be used in combination therapy with other drugs used for treating Alzheimer's disease. More particularly, the compound of Formula II, as well as pharmaceutically acceptable solvate thereof, may be used as an adjunct therapy in combination with acetylcholinesterase inhibitors, including but not limited to donepezil (CAS no 120014-06-4) and salts and solvates thereof, galantamine (CAS no 357-70-0) and salts and solvates thereof, rivastigmine (CAS no 123441-03-2) and salts and solvates thereof, tacrine (CAS no 321-64-2) and salts and solvates thereof, or in combination with NMDA glutamate receptor antagonists, including but not limited to memantine (CAS no 19982-08-2) and salts and solvates thereof, or in combination with dual acetylcholinesterase inhibitor and NMDA glutamate receptor antagonist, including but not limited to huperzine A (CAS no 102518-79-6) and salts and solvates thereof, or in combination with glucagon-like peptide 1 (GLP-1) agonists, including but not limited to liraglutide (CAS no 204656-20-2) and salts and solvates thereof, exenatide (CAS no 141732-76-5) and salts and solvates thereof, or in combination with retinoids, including but not limited to acitretin (CAS no 55079-83-9) and salts and solvates thereof, or in combination with calcium channel blockers (CCB), including but not limited to nilvadipine (CAS no 75530-68-6) and salts and solvates thereof, nitrendipine (CAS no 39562-70-4) and salts and solvates thereof, nimodipine (CAS no 66085-59-4) and salts and solvates thereof or in combination with angiotensin receptor blockers, including but not limited to valsartan (CAS no 137862-53-4) and salts and solvates thereof, or in combination with tetracycline antibiotics, including but not limited to minocycline (CAS no 10118-90-8) and salts and solvates thereof.

Thus, the methods of treatment and pharmaceutical compositions of the present invention may employ a sulphate salt of N-(3-(4-(3-(diisobutylamino)propyl)piperazin-1-yl)propyl)-1H-benzo[d]imidazol-2-amine or a pharmaceutically acceptable solvate thereof in monotherapy. However, said methods and compositions may also be used multiple therapy in which one or more sulphate salts of N-(3-(4-(3-(diisobutylamino)propyl)piperazin-1-yl)propyl)-1H-benzo[d]imidazol-2-amine or their pharmaceutically acceptable solvates are co-administered in combination with one or more other therapeutic agents.

In the above-described embodiment, combinations of sulphate salts of N-(3-(4-(3-(diisobutylamino)propyl)piperazin-1-yl)propyl)-1H-benzo[d]imidazol-2-amine or a pharmaceutically acceptable solvate thereof and other therapeutic active agents may be administered, in terms of dosage forms, either separately or in conjunction with each other, and in terms of their time of administration, either serially or simultaneously. Thus, the administration of one component agent may be prior to, concurrent with, or subsequent to the administration of the other component agent(s).

Generally, for pharmaceutical use, the sulphate salts of N-(3-(4-(3-(diisobutylamino)propyl)piperazin-1-yl)propyl)-1H-benzo[d]imidazol-2-amine or pharmaceutically acceptable solvates thereof may be formulated as a pharmaceutical composition comprising at least one sulphate salt of the invention or a pharmaceutically acceptable solvate thereof and at least one pharmaceutically acceptable carrier, diluent, excipient and/or adjuvant, and optionally one or more further therapeutic agents and/or active ingredients.

By means of non-limiting examples, pharmaceutical composition may be in a dosage form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences. The pharmaceutical compositions may be formulated in solid form and re-dissolved or suspended prior to use.

Some preferred, but non-limiting examples of dosage forms include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The pharmaceutical compositions can optionally contain other substances that are commonly used in pharmaceutical formulations, such as lubricating agents, wetting agents, emulsifying and suspending agents, dispersing agents, disintegrating agents, stabilizing agents, isotonic agents, bulking agents, fillers, preserving agents, sweetening agents, flavouring agents, perfuming agents, colouring agents, antibacterial agents and/or antifungal agents such as parabens, chlorobutanol, phenol, sorbic acid, dispensing agents, flow regulators, release agents, etc. The compositions may also be formulated so as to provide rapid, sustained or delayed release of the active compound(s) contained therein.

The pharmaceutical compositions of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 0.05 and 1000 mg, and usually between 1 and 500 mg, of the at least one compound of the invention, e.g. about 10, 25, 50, 100, 200, 300 or 400 mg per unit dosage.

Usually, depending on the condition to be prevented or treated and the route of administration, the active compound of the invention will usually be administered between 0.01 to 100 mg per kilogram, more often between 0.1 and 50 mg, such as between 1 and 25 mg, for example about 0.5, 1, 5, 10, 15, 20 or 25 mg, per kilogram body weight of the patient per day, which may be administered as a single daily dose, divided over one or more daily doses, or essentially continuously, e.g. using a drip infusion.

All references to compounds of Formula II include references to solvates, in particular compounds of Formula III, multi-component complexes and liquid crystals thereof.

The compounds disclosed throughout the present application were named using ChemDraw® Ultra version 12.0 (CambridgeSoft, Cambridge, Mass., USA).

N-(3-(4-(3-(diisobutylamino)propyl)piperazin-1-yl)propyl)-1H-benzo[d]imidazol-2-amine can be obtained as disclosed in WO2006/051489. The sulphate salts and solvates thereof can be prepared according to techniques known in the art such as those involving precipitation, crystallization, recrystallization, lyophilisation, phase transfer or ion exchange resins.

DEFINITIONS

The term "solvate" is used herein to describe a compound in this invention that contains stoichiometric or sub-stoichiometric amounts of one or more pharmaceutically acceptable solvent molecule such as ethanol. The term "hydrate" refers to when the said solvent is water. The pharmaceutically acceptable solvent molecules may be co-crystallized with the compound of the invention, and/or be present in crystalline and/or amorphous phases of solids thereof, and/or be adsorbed thereto.

The term "Alzheimer's disease" as used herein, designates all types of Alzheimer's disease, including but not limited to the sporadic and familial types.

The term "inclusion body myopathy with Paget's disease of bone and/or frontotemporal dementia (IBMPFD)" as used herein, is a type of myopathy, more specifically an inherited adult onset multisystem disease that affects muscle, bone and the central nervous system. Patients with this condition can present with a variety of manifestations, comprising inclusion body myopathy, Paget's Disease of the bone, frontotemporal dementia and/or amyotrophic lateral sclerosis (Lou Gehrig's disease).

The term "dementia with Lewy bodies (DLB)" as used herein, also known as Lewy body dementia, diffuse Lewy body disease, cortical Lewy body disease and senile dementia of Lewy type, is a type of dementia closely associated with both Alzheimer's and Parkinson's diseases. It is characterized by the presence of Lewy bodies, clumps of alpha-synuclein and ubiquitin protein in neurons, detectable in post mortem brain histology.

The term "synucleopathies" as used herein means a disease of the central nervous system characterized by alpha synuclein-positive depositions in neurons.

The term "amyloid angiopathies" as used herein means diseases related to amyloid deposits forming in the walls of the blood vessels of the central nervous system.

The term "tauopathies" as used herein means neurodegenerative diseases associated with the pathological aggregation of tau protein in the human brain.

The term "developmental diseases" as used herein means any condition that appears at some stage in a child's development and delays or prevent the development of one or more physiological functions such as language skills Developmental diseases include psychological and physical diseases. Non-limiting examples of developmental diseases are autism spectrum disorder (ASD), Down syndrome, attention deficit disorder (ADD) and attention deficit hyperactive disorder (ADHD).

The term "patient" refers to a warm-blooded animal, more preferably a human, who/which is awaiting the receipt of, or is receiving medical care or is/will be the object of a medical procedure.

The term "human" refers to a subject of both genders and at any stage of development (i.e. neonate, infant, juvenile, adolescent, adult).

The terms "treat", "treating" and "treatment, as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e.g. N-(3-(4-(3-(diisobutylamino)propyl)piperazin-1-yl)propyl)-1H-benzo[d]imidazol-2-amine) that is sufficient to achieve the desired therapeutic or prophylactic effect in the patient to which/whom it is administered.

The term "administration", or a variant thereof (e.g., "administering"), means providing the active agent or active ingredient (e.g. N-(3-(4-(3-(diisobutylamino)propyl)piperazin-1-yl)propyl)-1H-benzo[d]imidazol-2-amine), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

BRIEF DESCRIPTION OF THE DRAWINGS

FIG. 13-a shows photographs of crystals of N-(3-(4-(3-(diisobutylamino)propyl)piperazin-1-yl)propyl)-1H-benzo[d]imidazol-2-amine 4 eq oxalate salt, as observable with an optical microscope, at zoom ×325, under transmitted light.

FIG. 13-b shows photographs of crystals of N-(3-(4-(3-(diisobutylamino)propyl)piperazin-1-yl)propyl)-1H-benzo[d]imidazol-2-amine 4 eq oxalate salt, as observable with an optical microscope, at zoom ×325, under cross polarized light.

FIG. 14 shows the XRPD diffractogram of N-(3-(4-(3-(diisobutylamino)propyl)piperazin-1-yl)propyl)-1H-benzo[d]imidazol-2-amine, 2 eq sulphate salt of example 4.

FIGS. 19-a to 19-d show the results obtained for N-(3-(4-(3-(diisobutylamino)propyl)piperazin-1-yl)propyl)-1H-benzo[d]imidazol-2-amine, 1.8 eq sulphate salt in the in vitro APP metabolism assay. In all figures, the results are provided for the control (white bar) and the sulphate salt of the invention at four concentrations (black bars). FIG. 19-a shows the AICD levels, FIG. 19-b the CTFα levels, FIG. 19-c the Aβ$_{1-42}$ levels and FIG. 19-d the sAPPα levels.

FIG. 20 shows the CTFα levels measured in the frontal cortex of mice treated with various doses of N-(3-(4-(3-(diisobutylamino)propyl)piperazin-1-yl)propyl)-1H-benzo[d]imidazol-2-amine, 1.8 eq sulphate salt (in vivo APP metabolism assay; 24 h acute treatment). The results are provided for the vehicle (white bar) and the sulphate salt of the invention at five doses (dark grey bars).

FIG. 21 shows the CTFα levels measured in the frontal cortex of mice treated with various doses of N-(3-(4-(3-(diisobutylamino)propyl)piperazin-1-yl)propyl)-1H-benzo[d]imidazol-2-amine, 2 eq sulphate salt or of the oxalate salt of WO2006/051489 (in vivo APP metabolism assay; mice 24 h acute treatment). The results are provided for the vehicle (white bar), the oxalate salt (light grey bars) and the sulphate salt of the invention (dark grey bars) at 6 mg/kg.

FIGS. 22-a and 22-b show the results obtained for N-(3-(4-(3-(diisobutylamino)propyl)piperazin-1-yl)propyl)-1H-benzo[d]imidazol-2-amine, 1.8 eq sulphate salt in the in vivo APP metabolism assay (rats 1-month chronic study). In all figures, the results are provided for the vehicle (white bar) and the sulphate salt of the invention at two concentrations (dark grey bars). FIG. 22-a shows the CTF levels in the frontal cortex and FIG. 22-b the CTFβ levels in the hippocampus.

FIGS. 23-a, 23-b and 23-c show the results obtained for N-(3-(4-(3-(diisobutylamino)propyl)piperazin-1-yl)propyl)-1H-benzo[d]imidazol-2-amine, 1.8 eq sulphate salt in the in vivo APP metabolism assay (mice 3-months chronic study). In all figures, the results are provided for the vehicle (white bar) and the sulphate salt of the invention at three concentrations (dark grey bars). FIG. 23-a shows the AT100 levels, FIG. 23-b the AT8 levels, and FIG. 23-c the LPO levels.

CHEMISTRY EXAMPLES

Figure 1:
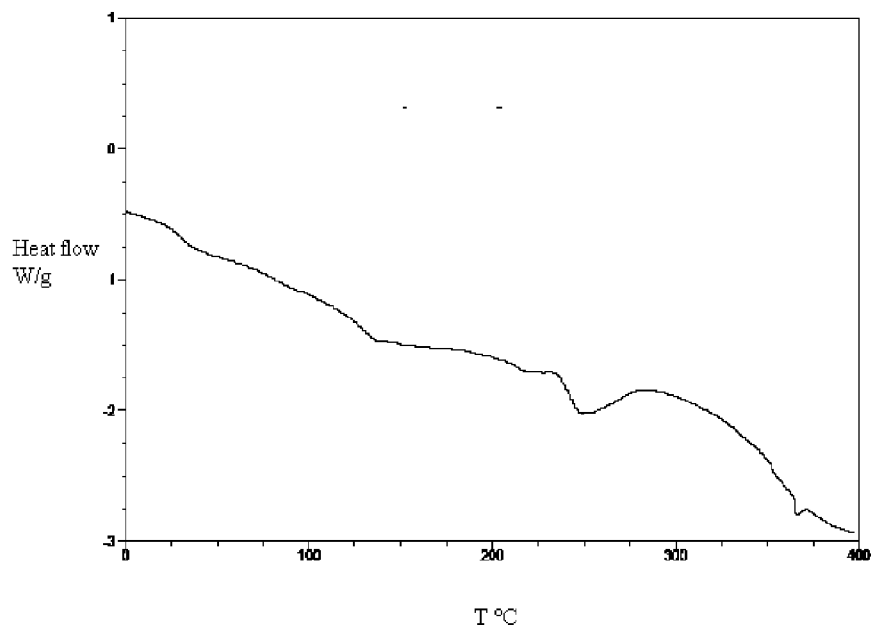
FIG. 1 shows the DSC spectrum of the tartrate salt (1 eq) of N-(3-(4-(3-(diisobutylamino)propyl)piperazin-1-yl)propyl)-1H-benzo[d]imidazol-2-amine.

The following abbreviations are used throughout the present application: ° C.: Celsius degrees, DIPE: di-isopropyl ether, DSC: differential scanning calorimetry, DVS: dynamic water vapour sorption/desorption, δ: NMR chemical shifts expressed in ppm, eq: equivalent(s), Et: ethyl, g: gram(s), h: hour(s), HPLC: high performance liquid chromatography, IPA: isopropanol, IR: infrared, L: liter(s), LCMS: HPLC coupled to a mass spectrometer, M: mol/L, mM: mmol/L, μM: μmol/L, Me: methyl, mg: milligram(s), min: minute(s), mL: milliliter(s), mol: mole(s), mmol: millimole(s), μmol: micromole(s), MS: Mass Spectrometry, NMR: nuclear magnetic resonance, ppm: party per million, RH: relative humidity, rm: reaction mixture, rpm: round(s) per minute, rt: retention time, RT: room temperature (ca 15-25° C.), RV: reaction vessel, THF: tetrahydrofuran, XRPD: X ray powder diffraction, W: Watt(s).

All reported temperatures are expressed in degrees Celsius (° C.); all reactions were carried out at room temperature (RT) unless otherwise stated.

Experimental set-up or purification procedures that were used in this invention, when not described in specific details, are assumed to be known to those conversant in the art and are described in such standard reference manuals as: i) Gordon, A. J.; Ford, R. A. "The Chemist's Companion—A Handbook of Practical Data, Techniques, and References", Wiley: New York, 1972; ii) Vogel's Textbook of Practical Organic Chemistry, Pearson Prentice Hall: London, 1989.

HPLC Analysis.

Method A:

HPLC spectra were typically obtained on a Waters Alliance 2695 system HPLC. The instrument includes an autosampler, a quaternary pump, and an ultraviolet multi-wavelength detector. The chromatography column used was a Waters X-Terra RP18 5 μm, 4.6×250 mm.

Eluent typically used was a mixture of solution A (0.1% TFA in $H_2O$) and solution B (0.1% TFA in MeOH).

Gradient was applied at a flow rate of 1 mL per minute as follows: gradient held the initial conditions of 5% solution B for 0 min, increased linearly to 40% solution B in 50 min, held at 40% during 5 min, returned to initial conditions in 1 min and maintained for 5 min.

Method B:

In a variant, HPLC analyses were carried out according to the parameters disclosed in Table 1 below.

TABLE 1

| HPLC parameters for method B | | | |
|---|---|---|---|
| HPLC equipment | Injector/pump: Waters Alliance 2695 Detector: Waters Photo Diode Array 996 Software: Waters Millenium | | |
| Column | SymmetryShield C18 150 mm × 4.6 mmm – dp = 5 μm | | |
| Mobile phase | A: $H_2O$/TFA 0.05% B: MeOH/TFA 0.05% | | |
| | Time | A % | B % |
| | 0 | 95 | 5 |
| | 5 | 95 | 5 |
| | 20 | 10 | 90 |
| | 25 | 10 | 90 |
| | 25.1 | 95 | 5 |
| | 30 | 95 | 5 |
| Flow rate | 1 mL/min | | |
| Column temperature | Room temperature | | |
| Detection | UV: λ = 276 nm | | |
| Test solution | Suitable dilution in $H_2O$/$CH_3CN$ 50/50 (v/v) | | |
| Injection volume | 5 μL | | |
| Injector temperature | 20° C. | | |
| Retention time | Free base ~13 min | | |

NMR Analysis $^1H$ (300 MHz) spectra were recorded on a Bruker Advance DRX 300 MHz instrument. Chemical shifts are expressed in parts per million, (ppm, δ units). Coupling constants are expressed in Hertz (Hz). Abbreviations for multiplicities observed in NMR spectra are as follows: s (singlet), d (doublet), t (triplet), q (quadruplet), m (multiplet), br (broad).

DSC Spectra.

TA Instrument, DSC Q10.

DSC spectra were recorded on a TA DSC Q10 instrument within a temperature range of −10° C. to 300° C. or 400° C. and with 10° C. increments.

Optical Microscopy.

Observation by optical microscopy was performed on a LEICA DMIRB microscope equipped with a digital camera and a motorized stage. A few powder grains are dispersed on a glass plate with mineral oil. Photos were recorded with a picture analysis platform from Microvision Instruments, both under transmitted light and polarized light.

X-Ray Powder Diffraction

X-ray powder diffraction (XRPD) analysis is performed on a Brüker—AXS D8 Advance diffractometer, using a copper anti-cathode, a mono-crystalline silicon sample holder and a position sensitive detector. Instrument operating conditions for X-rays pattern acquisition are described in Table 2.

TABLE 2

| Instrument operating conditions for X-rays profile acquisition | | |
|---|---|---|
| Temperature | | Ambient |
| Atmosphere | | Ambient |
| X-rays generator | voltage (kV) | 40 |
| | intensity (mA) | 40 |
| X-rays source | target | Cu |
| | emission radiation $K\lambda_1$ (nm) | 0.15406 |
| | $K\lambda_2$ (nm) | 0.15444 |
| | Ratio $K\lambda_2/K\lambda_1$ | 0.5 |
| | Kβ filter | Ni |
| Slit (nm) | anti-divergence | 0.6 |
| Goniometer | angular sector analyzed (° for 2θ) | 5-70 |
| | step size (° for 2θ) | 0.0714 |
| Rotation speed for sample holder (rpm) | | 30 |
| Detection | angular opening (θ) | 8 |
| | step time for measuring diffracted intensity (s) | 6 |

The powder sample is dispersed on the silicon sample holder in a way to avoid preferred orientation (not randomly oriented crystals) and to ensure planarity of the specimen surface.

Dynamic Vapour Sorption

Dynamic vapour sorption (DVS) analyses with water were performed on a DVS-Intrisic incubator from SMS Ltd, equipped with DVS-Intrisic Control Software 1.0.

A sample of about 5 to 10 mg, placed in an aluminium pan holder, was submitted to a full-cycle analysis (sorption followed by desorption) under the conditions described in Table 3.

TABLE 3

| operating conditions for DVS analysis | |
|---|---|
| Temperature | 25° C. |
| Carrier gas rate | Dried and filtered air at 100 mL · $min^{-1}$ |
| Mode and criterion | dm/dt ≤ 0.002% · $min^{-1}$ |
| Humidity range | 0 to 95% RH |
| RH step | 5% |
| Minumum step time | 10 min |
| Maximum step time | 360 min |

The sample was pre-dried under a stream of dry filtered air until a stable mass was obtained. Relative humidity was then increased by 5% increments. At each step, the sample was allowed to increase until equilibrium is reached (dm/dt criterion), then relative humidity was increased further. Relative humidity was ramped up to 95%. After equilibration at this stage, desorption is started in a similar stepwise manner, with a sample weight allowed to stabilize after each incremental humidity decrease step.

Solvents and reagents were purchased and used as received from commercial vendors unless otherwise specified.

Example 1

Synthesis of N-(3-(4-(3-(diisobutylamino)propyl)piperazin-1-yl)propyl)-1H-benzo[d]imidazol-2-amine, 2.9 eq Sulphate Salt A diluted sulphuric acid solution in DIPE was prepared by adding 4 mL (0.0751 mol) of concentrated sulphuric acid to 28 mL (0.197 mol) of DIPE.

To a suspension of N-(3-(4-(3-(diisobutylamino)propyl)piperazin-1-yl)propyl)-1H-benzo[d]imidazol-2-amine (16.1 g, 0.03756 mol) in DIPE (280 mL), was added dropwise 32 mL of the above-described diluted sulphuric acid solution. A slight temperature increase around 10° C. was observed. The reaction mixture was stirred at RT and became limpid over an hour. The resulting white solution was filtered and recovered. The white powder obtained was then dried under vacuum at 50° C. during 48 hours.

Analytical Data

HPLC (method A): rt: 20.24 min;

Elemental Analysis:

calculated: % C=48.06; % H=7.74; N=13.45; % S=10.26; %O=20.48 experimental: % C=41.43; % H=6.95; % N=11.60%; % S=12.34; %O=26.53.

Example 2

Synthesis of N-(3-(4-(3-(diisobutylamino)propyl)piperazin-1-yl)propyl)-1H-benzo[d]imidazol-2-amine, 1.8 eq Sulphate Salt Title compound was prepared according to a similar procedure as the one described at example 1.

Analytical Data

HPLC (method A): rt: 29.207 min;

NMR (D$_2$O): δ (ppm): 7.2 (m, 4H, 2C$\underline{H}$); 3.7 (b, 8H, 4C$\underline{H}_2$); 3.4-3.1 (m, 8H, 4CH$_2$); 2.9 (m 4H, 2C$\underline{H}_2$); 2.3-1.9 (m, 6H, 2C$\underline{H}$+2C$\underline{H}_2$); 0.85 (d, 12H, 4CH$_3$).

Elemental Analysis:

calculated: % C=48.06; % H=7.74; N=13.45; % S=10.26; %O=20.48 experimental: % C=49.55; % H=7.89; N=13.87; % S=8.95; %O=19.29.

Example 3

Synthesis of N-(3-(4-(3-(diisobutylamino)propyl)piperazin-1-yl)propyl)-1H-benzo[d]imidazol-2-amine, 1 eq Sulphate Salt 3 mL of ethanol were added to 99.6 mg of synthesis of N-(3-(4-(3-(diisobutylamino)propyl)piperazin-1-yl)propyl)-1H-benzo[d]imidazol-2-amine, almost complete dissolution was achieved upon heating at 70° C. An equimolar quantity of a 0.5 M aqueous solution of sulphuric acid was added (465 μL) and full dissolution was observed. The solution is dried in vacuo at 70° C. to give a solid residue. The solid is re-suspended in IPA/EtOH at 70° C. to provide a suspension of fine particles; the solvent volume was then partially reduced under vacuum. The suspension was allowed to cool to room temperature. The supernatant was removed and the powder was dried under vacuum for 2 h at 70° C., to yield title compound in 89% yield.

HPLC analyses (method B): the percentage of N-(3-(4-(3-(diisobutylamino)propyl)piperazin-1-yl)propyl)-1H-benzo[d]imidazol-2-amine (free base) in title compound, determined by external standardization, was found to be 83.4%. This result was consistent with the theoretical calculated percent: 81.4%.

Example 4

Synthesis of N-(3-(4-(3-(diisobutylamino)propyl)piperazin-1-yl)propyl)-1H-benzo[d]imidazol-2-amine, 2 eq Sulphate Salt 3 mL of ethanol were added to 101.7 mg of synthesis of N-(3-(4-(3-(diisobutylamino)propyl)piperazin-1-yl)propyl)-1H-benzo[d]imidazol-2-amine, almost complete dissolution was achieved upon heating at 70° C. A two-molar quantity of a 0.5 M aqueous solution of sulphuric acid was added (950 μL) and full dissolution was observed. The solution is dried in vacuo at 70° C. to give a translucent film wherein crystallization of expected salt progressively occurred. The solid was then re-suspended in 3 mL of methanol to give a clear suspension which is stirred at 60° C. for 15 minutes. 10 mL of IPA were added to finalize salt crystallization and the resulting suspension was stirred at 80° C. for 30 minutes. The suspension was then allowed to cool to room temperature and stored overnight at sub-ambient temperature. The supernatant was removed from the flask and the powder dried in vacuo for 2.5 hours at 70° C. to provide title compound in 71% yield.

HPLC analyses (method B): the percentage of N-(3-(4-(3-(diisobutylamino)propyl)piperazin-1-yl)propyl)-1H-benzo[d]imidazol-2-amine (free base) in title compound, determined by external standardization, was found to be 65.8%. This result was consistent with the theoretical calculated percent: 68.6%.

No long term instability due to oxidation, in particular oxidation at the piperazine ring, was observed with sulphate salts in solid state.

Example 5

Physico-Chemical Analysis of Different Salts

The hydrochloride, hydrobromide, acetate, tartrate, fumarate, malate, oxalate and sulphate salts of N-(3-(4-(3-(diisobutylamino)propyl)piperazin-1-yl)propyl)-1H-benzo[d]imidazol-2-amine were prepared according to procedures similar to those described in the previous examples or standard salt formation methods well known in the art. The results of these salt formations are reported in Table 4.

TABLE 4

| salt formation results | | |
| --- | --- | --- |
| Salt | Acid eq. added | Physical form |
| Free base | 0 | Amorphous powder |
| Chloride | 4 | Precipitation of a very |

TABLE 4-continued salt formation results

| Salt | Acid eq. added | Physical form |
|---|---|---|
| Bromide | 1.1 | hygroscopic solid[1]<br>No solid formed |
| Acetate | 1 | No solid formed, oily residue |
| Acetate | 2 | No solid formed, oily residue |
| Fumarate | 1 | Not crystalline[2] |
| Tartrate[3] | 1 | Not crystalline[2] |
| Malate | 1 | Powder |
| Oxalate | 2 | Gum |
| Oxalate | 3 | Gum |
| Oxalate | 4 | Crystalline powder |
| Sulphate | 1 | Crystalline powder (colorless solid) |
| Sulphate | 2 | Crystalline powder (colorless solid) |

Figure 2:
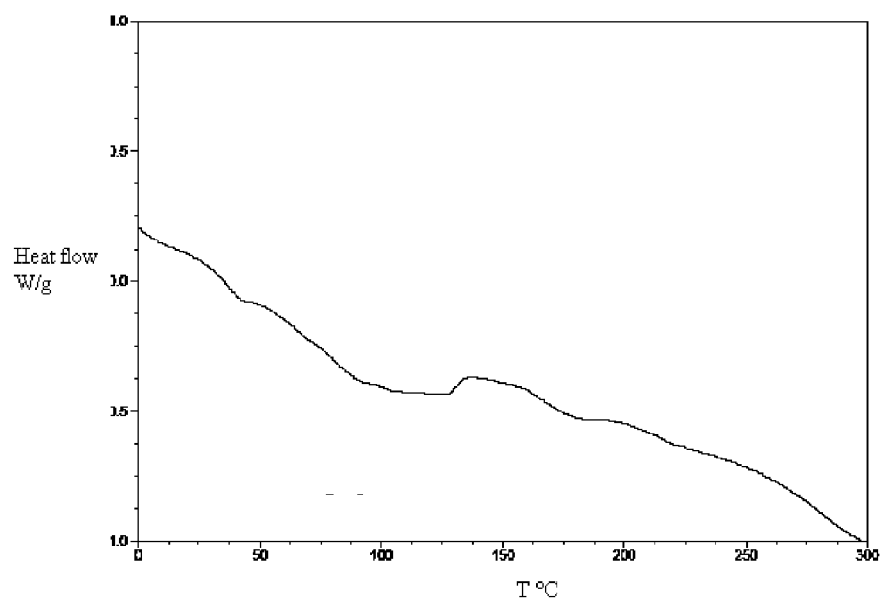
FIG. 2 shows the DSC spectrum of the fumarate salt (1 eq) of N-(3-(4-(3-(diisobutylamino)propyl)piperazin-1-yl)propyl)-1H-benzo[d]imidazol-2-amine.

[1] a weighed out sample of chloride salt was left standing open to the air. Said sample rapidly gained weight and eventually became deliquescent within a few seconds or minutes, depending on the room RH.
[2] DSC spectrum did not reveal any endotherm and is thus characteristic of solids lacking a crystalline phase
[3] salt formed in EtOH/water The chloride salt was straightforwardly found very hygroscopic while acetate salts were not obtained in solid form. Although tartrate and fumarate salts were obtained as solids, the DSC analysis showed that they are not crystalline (see FIGS. 1 and 2). Such deficiency can result in batch to batch variations with respect to solid forms. Batch to batch reproducibility is an essential criterion in the synthesis of drug compounds especially when different solid forms can have different pharmacokinetics and pharmacodynamics properties. Hence, tartrate and fumarate salts are not satisfactory.

Figure 3:
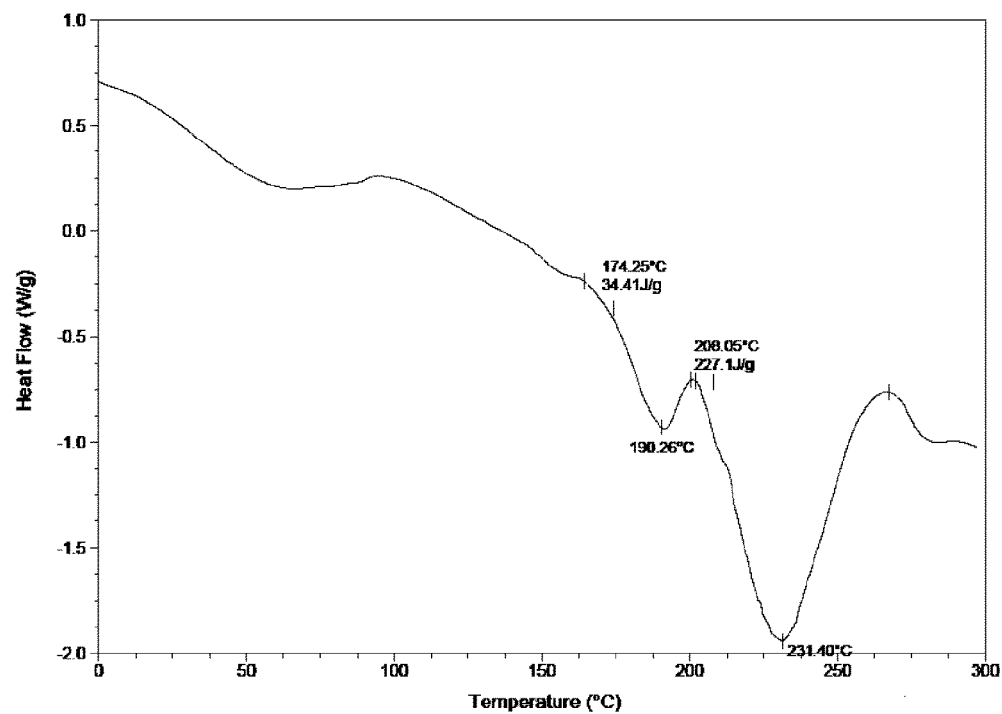
FIG. 3 shows the DSC spectrum of the oxalate salt (2 eq) of N-(3-(4-(3-(diisobutylamino)propyl)piperazin-1-yl)propyl)-1H-benzo[d]imidazol-2-amine.
Figure 4:
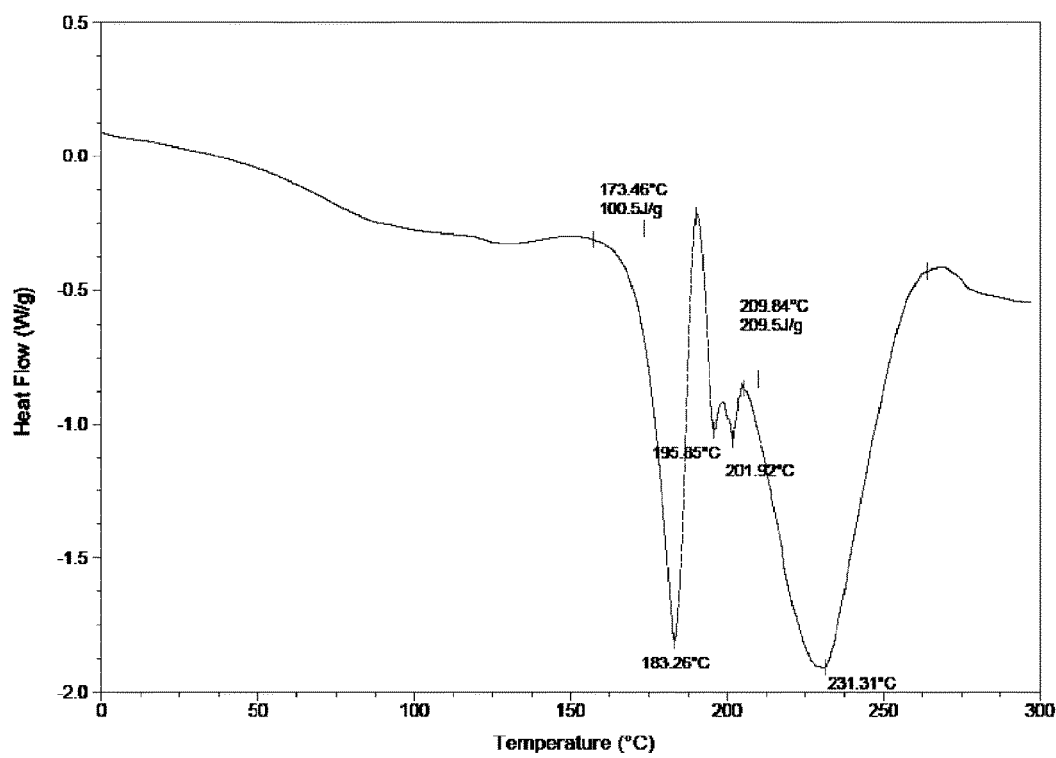
FIG. 4 shows the DSC spectrum of the oxalate salt (3 eq) of N-(3-(4-(3-(diisobutylamino)propyl)piperazin-1-yl)propyl)-1H-benzo[d]imidazol-2-amine.
Figure 5:
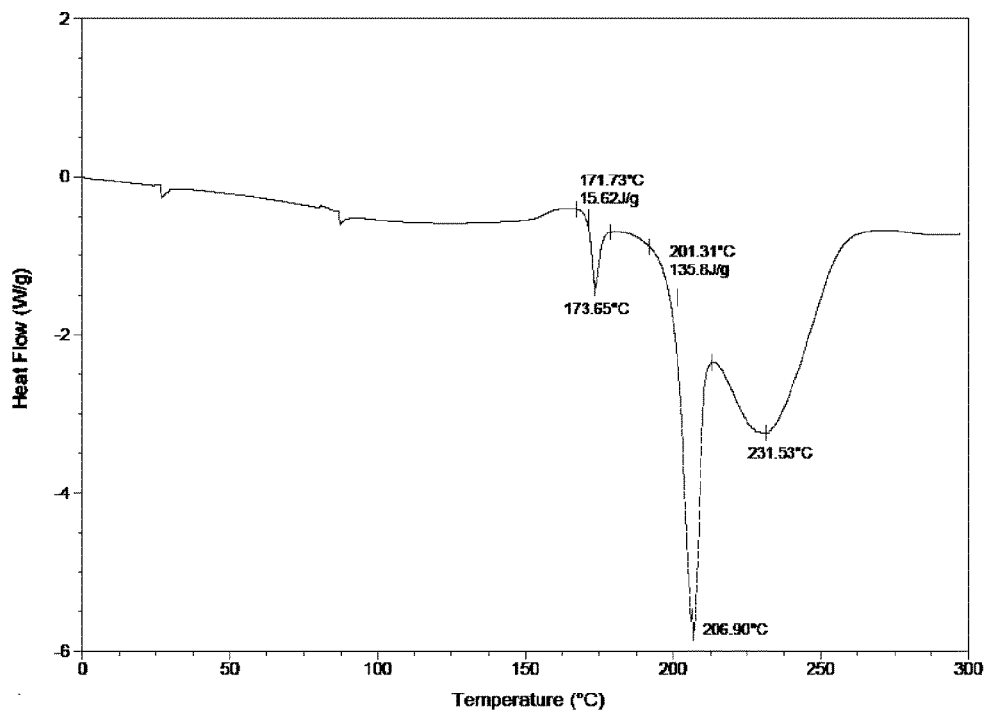
FIG. 5 shows the DSC spectrum of the oxalate salt (4 eq) of N-(3-(4-(3-(diisobutylamino)propyl)piperazin-1-yl)propyl)-1H-benzo[d]imidazol-2-amine.

The malate salt was obtained as a powder; however it bears an asymmetric carbon. Chiral centers considerably complicate clinical development since each stereoisomer needs to be equally characterized as the active stereoisomer. With regards to oxalate salts, 4 eq of oxalate counter-ions are required to obtain suitable crystalline powders. The DSC graphs of oxalate salts (2 eq, 3 eq and 4 eq) are shown respectively in FIGS. 3, 4 and 5. As shown by the DSC spectra the tetraoxalate salt bear the most well shaped and defined endotherm. The requirement of having 4 equivalents of oxalate salt is a caveat since the weight percentage of active molecule drops to as low as 54%. The amount of drug to be administered for a given dose of PAM is thus significantly increased as well as the risk of nephrotoxicity associated to oxalates.

Figure 6:
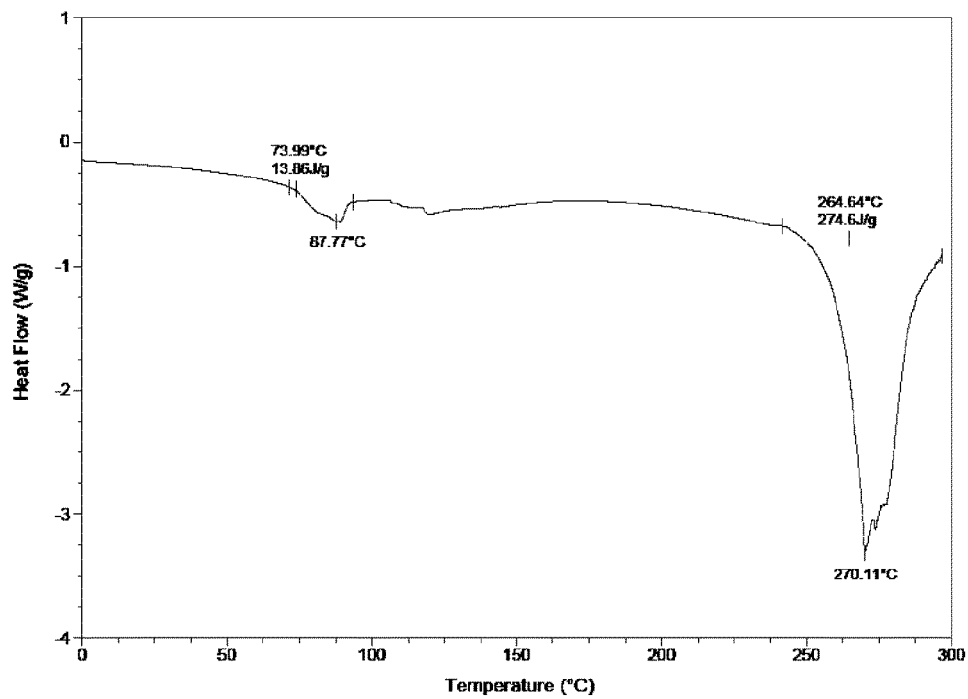
FIG. 6 shows the DSC spectrum of the sulphate salt (1 eq) of N-(3-(4-(3-(diisobutylamino)propyl)piperazin-1-yl)propyl)-1H-benzo[d]imidazol-2-amine.
Figure 7:
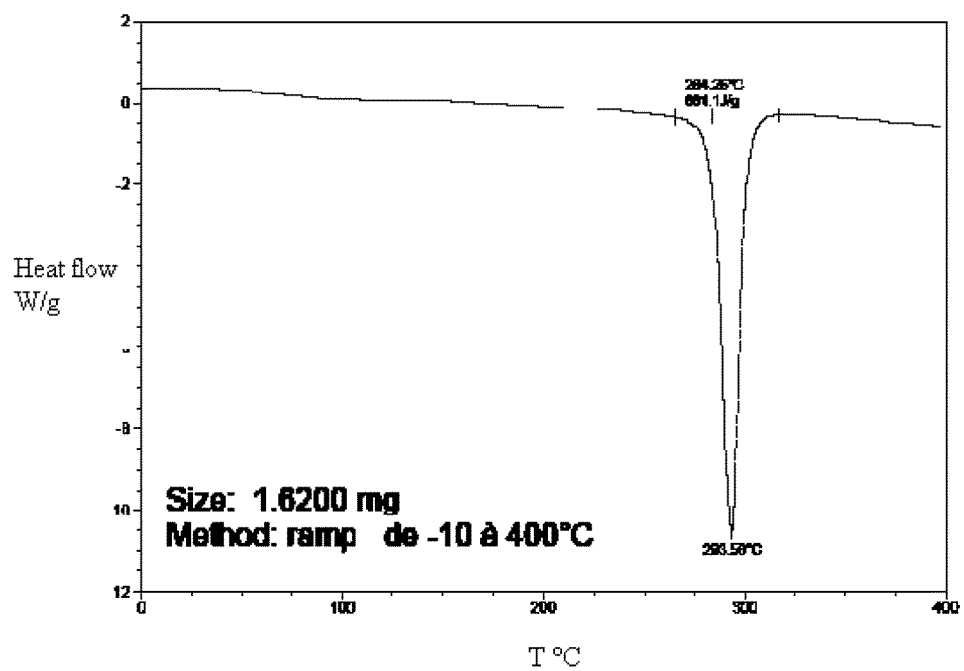
FIG. 7 shows the DSC spectrum of the sulphate salt (2 eq) of N-(3-(4-(3-(diisobutylamino)propyl)piperazin-1-yl)propyl)-1H-benzo[d]imidazol-2-amine.

Both sulphate salts precipitated as solids. They were found stable when left open to the air. In contrast to the chloride salt, no hygroscopicity issue was observed. The DSC analysis (see FIGS. 6 and 7) revealed well defined endotherms which are consistent with solids comprising a crystalline phase.

Example 6

XRPD Analysis of Oxalate and Sulphate Salts

Figure 8:
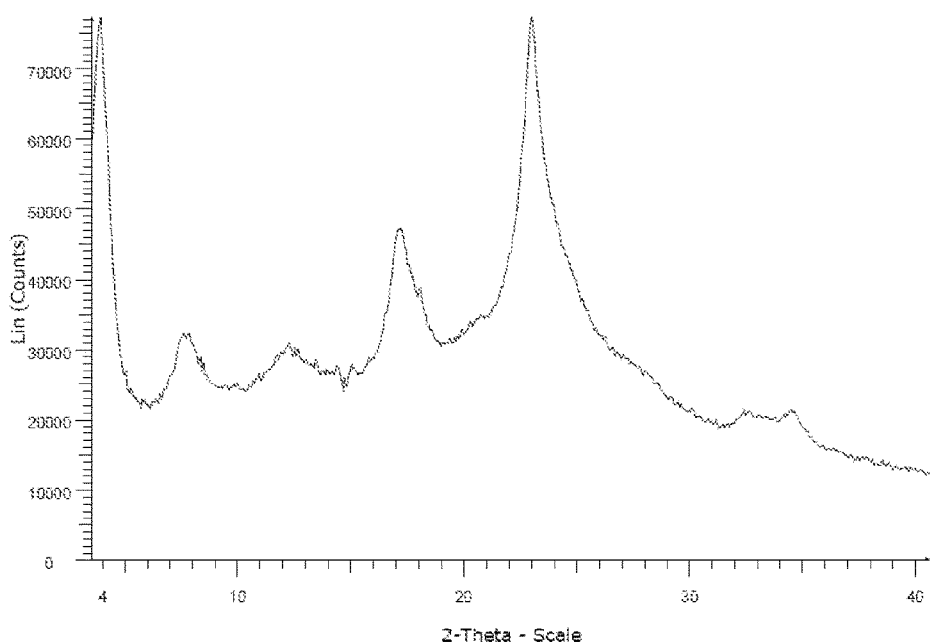
FIG. 8 shows the XRPD diffractogram of N-(3-(4-(3-(diisobutylamino)propyl)piperazin-1-yl)propyl)-1H-benzo[d]imidazol-2-amine, 4 eq oxalate salt.

The XRPD diffractogram of N-(3-(4-(3-(diisobutylamino) propyl)piperazin-1-yl)propyl)-1H-benzo[d]imidazol-2-amine, 4 eq oxalate salt is shown on FIG. 8. In the angular window analyzed, a few large diffraction rays of low intensity were detected. The XRPD profile reveals the presence of a high diffusion background. Such a XPRD profile is characteristic of a powder having a crystalline phase with little or poor crystallinity (large rays) with the presence of an amorphous phase (high diffusion background).

Figure 9:
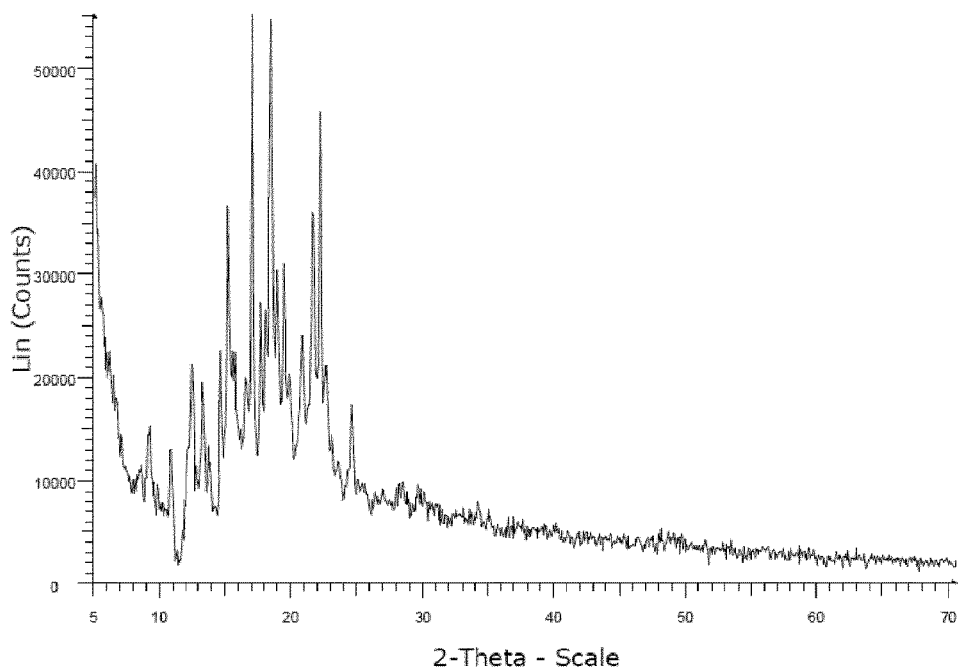
FIG. 9 shows the XRPD diffractogram of N-(3-(4-(3-(diisobutylamino)propyl)piperazin-1-yl)propyl)-1H-benzo[d]imidazol-2-amine, 2.9 eq sulphate salt of example 1.
Figure 10:
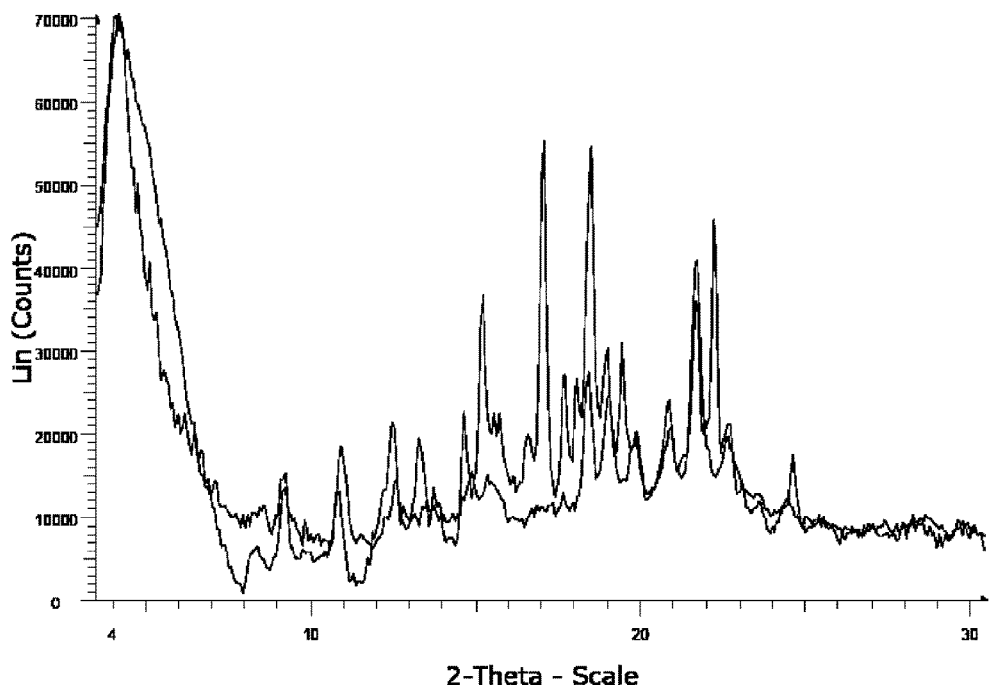
FIG. 10 shows the XRPD diffractogram of N-(3-(4-(3-(diisobutylamino)propyl)piperazin-1-yl)propyl)-1H-benzo[d]imidazol-2-amine, 1.8 eq sulphate salt of example 2 (higher intensity graph) superimposed with the one of N-(3-(4-(3-(diisobutylamino)propyl)piperazin-1-yl)propyl)-1H-benzo[d]imidazol-2-amine, 2.9 eq sulphate salt of example 1 (lower intensity graph).

The X-Ray diffraction profile for the sulphate salt of example 1 (see FIG. 9) shows several well-defined and sharp diffraction peaks between 5 and 25° in 2-theta scale, indicating that the solid form of said sulphate salt comprises a well good crystalline phase. The diffractogram also presents a background halo (between 10 and 30°) that is interpreted as coming from an amorphous fraction present in the solid. Profiles comparison with the sulphate salt of example 2 reveal many overlapping between the several diffraction peaks detected (see FIG. 10).

Figure 11:
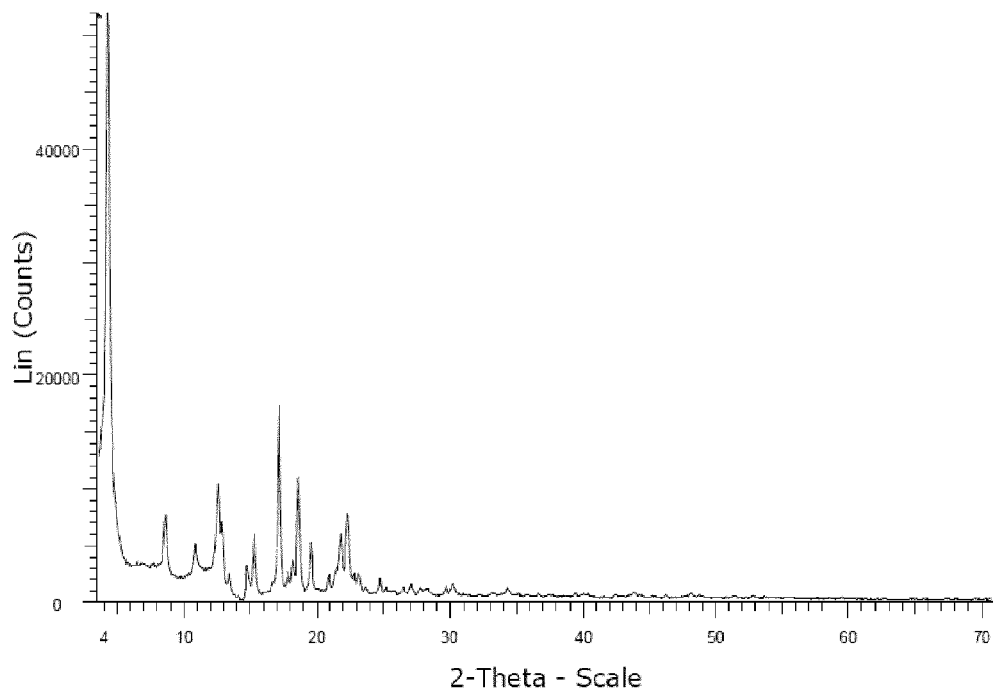
FIG. 11 shows the XRPD diffractogram of N-(3-(4-(3-(diisobutylamino)propyl)piperazin-1-yl)propyl)-1H-benzo[d]imidazol-2-amine, 1 eq sulphate salt of example 3.
Figure 12:
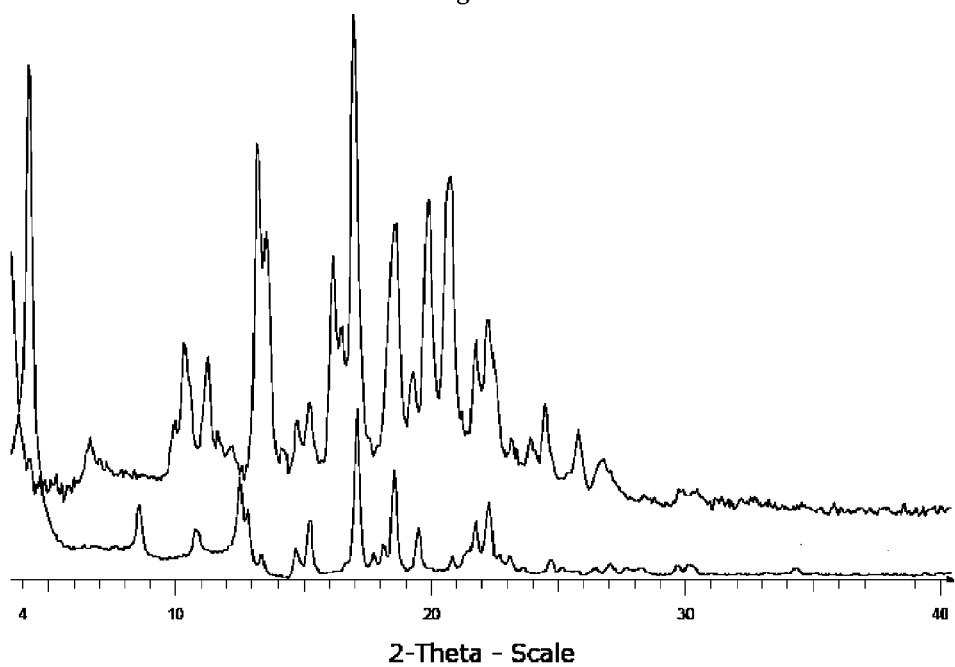
FIG. 12 shows the XRPD diffractogram of N-(3-(4-(3-(diisobutylamino)propyl)piperazin-1-yl)propyl)-1H-benzo[d]imidazol-2-amine, 1 eq sulphate salt of example 3 (bottom graph) superimposed with the one of N-(3-(4-(3-(diisobutylamino)propyl)piperazin-1-yl)propyl)-1H-benzo[d]imidazol-2-amine (free base) (top graph).

The XPRD diffractogram of the sulphate salt of example 3 (see FIG. 11) confirmed the good crystallinity of this salt with numerous, fine and well defined diffraction peaks between 4 and 30° 2θ, and reported a different diffraction profile from synthesis of N-(3-(4-(3-(diisobutylamino)propyl)piperazin-1-yl)propyl)-1H-benzo[d]imidazol-2-amine (free base). The XPRD profile of this salt has been compared with the one of the free base, both profiles superimposed in a same chromatograph (FIG. 12) are consistent with different crystal forms between the sulphate salt and the free base. These results are consistent with the observations by optical microscopy. Indeed, the high birefringence and the well defined stick-like morphology of particles when observed under transmitted light (FIG. 13a) and cross polarized light (FIG. 13b) indicated a sulphate salt of good crystallinity.

Figure 15:
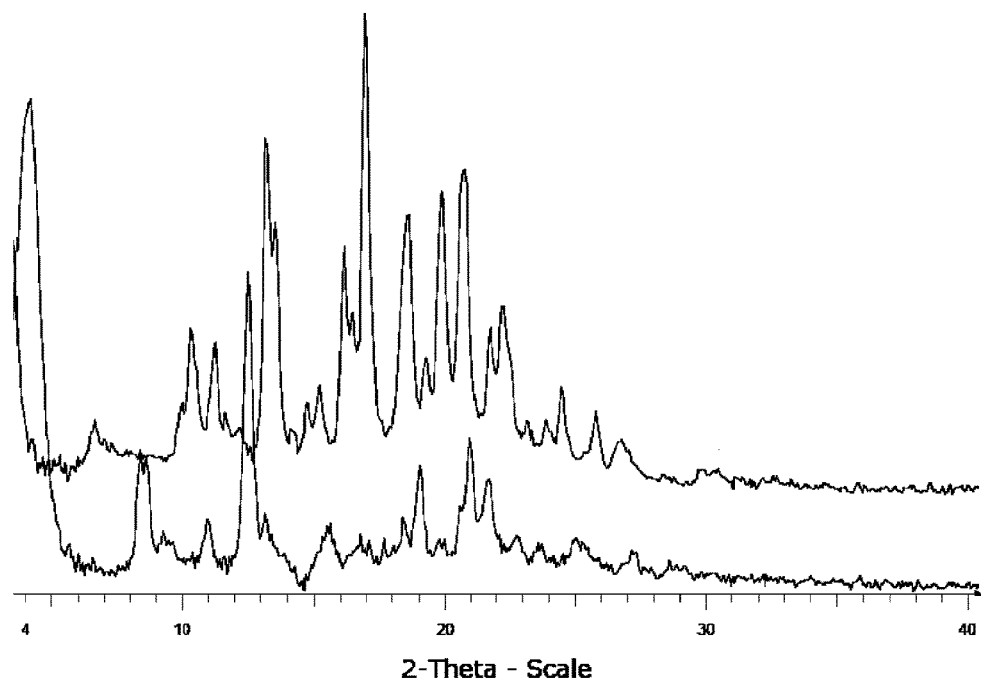
FIG. 15 shows the XRPD diffractogram of N-(3-(4-(3-(diisobutylamino)propyl)piperazin-1-yl)propyl)-1H-benzo[d]imidazol-2-amine, 2 eq sulphate salt of example 4 (bottom graph) superimposed with the one of N-(3-(4-(3-(diisobutylamino)propyl)piperazin-1-yl)propyl)-1H-benzo[d]imidazol-2-amine (free base) (top graph).

The XPRD diffractogram of the sulphate salt of example 4 (see FIG. 14) confirmed the good crystallinity of this salt with numerous diffraction peaks between 4 and 30° 2θ, and reported a different diffraction profile from synthesis of N-(3-(4-(3-(diisobutylamino)propyl)piperazin-1-yl)propyl)-1H-benzo[d]imidazol-2-amine (free base). The XPRD profile of this salt has been compared with the one of the free base, both profiles superimposed in a same chromatograph (FIG. 15) are consistent with different crystal forms between the sulphate salt and the free base.

As a result, Examples 5 and 6 clearly show that sulphate salts are superior to any other acid salt and to oxalate salts in particular. Sulphate salts do not bear severe hygroscopicity as chloride salts. Unlike bromide salts, they crystallize to provide powder materials. Their crystallinity is indeed far superior to those of tartrate and fumarate salts. Like sulphate salts, the oxalate salt with a specific 4 eq stoichiometry provides solids that comprise a crystalline and an amorphous phase. However, the XRPD profiles and optical microscopy under transmitted and polarized lights revealed that the crystalline phase of sulphate salts is better defined in terms of morphology and crystallinity than the one of the oxalate salt. Moreover, sulphate salts remedy the shortcomings of N-(3-(4-(3-(diisobutylamino)propyl)piperazin-1-yl)propyl)-1H-benzo[d]imidazol-2-amine (free base), i.e. they can be isolated in a solid form having a crystallized phase with a good crystallinity and have no obvious stability issues. Furthermore, they broaden the formulation possibilities of this PAM owing to their very high water solubility. The 4 eq oxalate salt did not fully remedy the shortcomings of the free base in terms of crystallinity and morphology and are anyway inferior to sulphate salts in these aspects. The skilled person would even consider a 4 eq oxalate salt as worsening the overall properties of the free base PAM since it contains high quantities of oxalate counter-ions which can induce severe nephrotoxicity.

Example 7

DVS profile of N-(3-(4-(3-(diisobutylamino)propyl) piperazin-1-yl)propyl)-1H-benzo[d]imidazol-2-amine, 1 eq Sulphate Salt DVS analysis was carried out according to the method described above.

Figure 16:
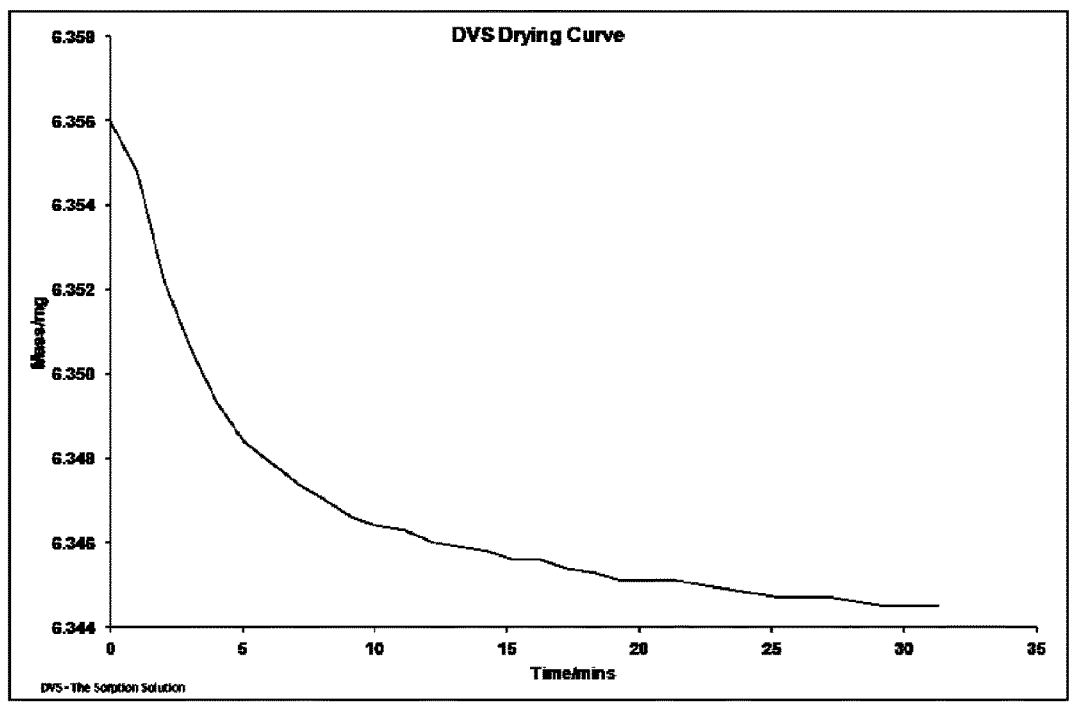
FIG. 16 shows the DVS drying curve at 25° C. of N-(3-(4-(3-(diisobutylamino)propyl)piperazin-1-yl)propyl)-1H-benzo[d]imidazol-2-amine, 1 eq sulphate salt of example 3.
Figure 17:
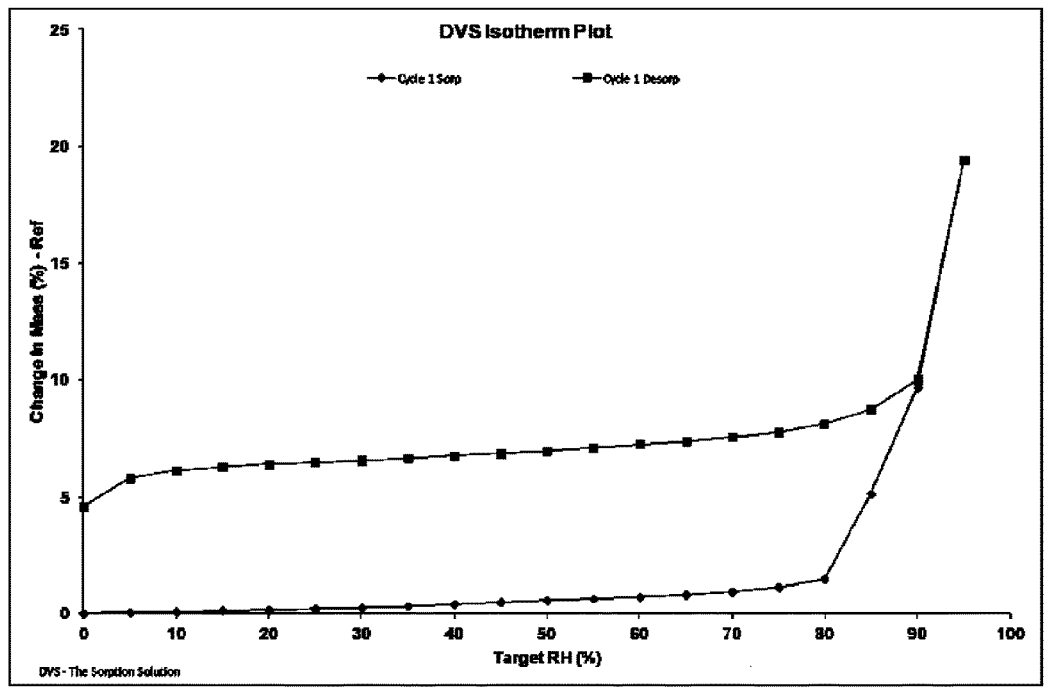
FIG. 17 shows the DVS isotherm sorption/desorption plots at 25° C. of N-(3-(4-(3-(diisobutylamino)propyl)piperazin-1-yl)propyl)-1H-benzo[d]imidazol-2-amine, 1 eq sulphate salt of example 3.

The results are shown in FIGS. 16 and 17 which display the DVS drying curve as well as the DVS isotherm plots (water vapour sorption/desorption traces) after preliminary drying of the sulphate salt of example 3. In FIG. 17, the top curve corresponds to the desorption phase and bottom curve to the sorption phase.

Upon drying at 25° C./0% RH, the sample lost 0.18% of its mass.

Upon sorption, three relative humidity intervals corresponding to different water sorption rates and behaviours were observed from the sample mass variation:
- from 0 to 80% RH: continuous and slow water sorption rate; water uptake at 25° C./60% RH and 25° C./80% RH were respectively of 0.7% and 1.5% compared to the sample mass obtained after initial drying at 0% RH;
- from 80 to 90% RH: rapid and nearly constant water sorption rate; water uptake at 25° C./90% RH was 9.7% compared to the sample mass obtained after initial drying at 0% RH;
- water sorption then further increased and water vapour uptake at 25° C./95% RH was of 19.4% compared to the sample mass obtained after initial drying at 0% RH.

Upon desorption, three relative humidity intervals corresponding to different water sorption rates and behaviours were observed:
- from 95 to 90% RH: rapid decrease of the residual water rate with 10% remaining at 25° C./75% RH compared to the sample mass obtained after initial drying at 0% RH;
- from 75 to 10% RH: the sample retained the "adsorbed" water with a strong and nearly constant hysteresis (up to 6.7% at 25° C./75% RH);
- from 10 to 0% RH: the sample lost part of its water; the remaining amount of water was 4.6% at 25° C./0% RH, compared to the sample mass obtained after initial drying at 0% RH; at this stage the sample mass was stabilized and thus in equilibrium with the surrounding environment.

Based on commonly used criteria (i.e. a compound is said hygroscopic if it presents more than 2% by weight water uptake at 25° C./60% RH), the sulphate salt of example 3 was not hygroscopic at 25° C./60% RH, with only an overall mass uptake at this stage.

Given the rapid water uptake at 80% RH, as well as the strong hysteresis (6 to 6.7% of water remaining from 80 to 10% RH upon desorption), the sulphate salt of example 3, originally obtained as its non-solvated form, converted into a di-hydrated form at high RH. The theoretical water uptake for the di-hydrated form of N-(3-(4-(3-(diisobutylamino) propyl)piperazin-1-yl)propyl)-1H-benzo[d]imidazol-2-amine, 1 eq sulphate salt of example 3 is 6.8% and in line with experimentally determined 6.7%.

Figure 18:
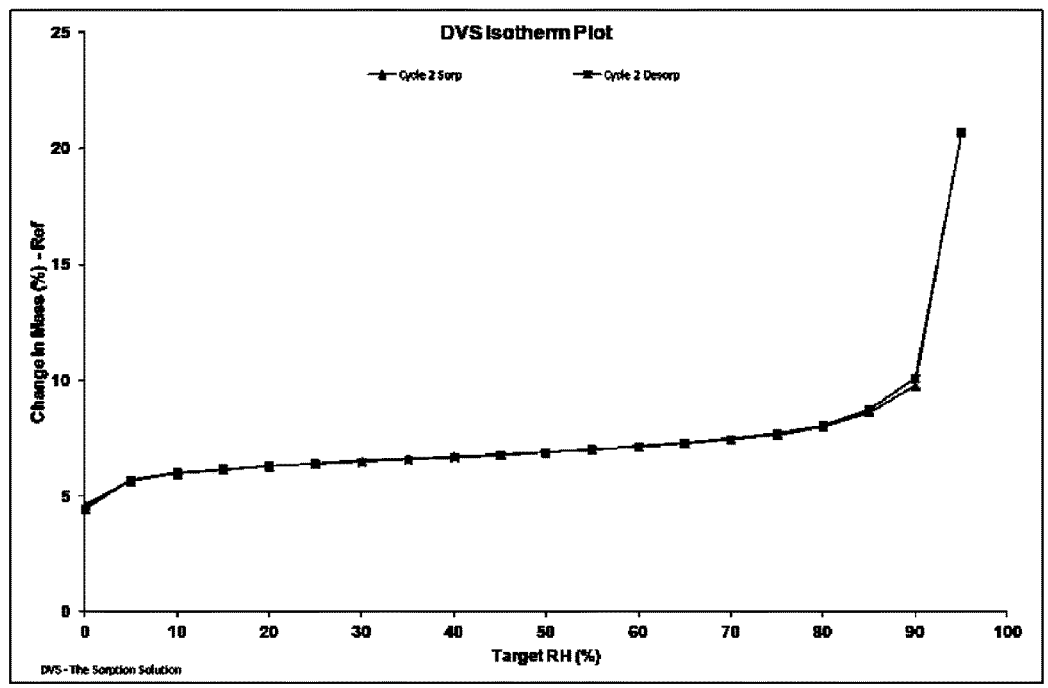
FIG. 18 shows the DVS isotherm sorption/desorption plots at 25° C. of the dehydrated form of N-(3-(4-(3-(diisobutylamino)propyl)piperazin-1-yl)propyl)-1H-benzo[d]imidazol-2-amine, 1 eq sulphate salt of example 3.

At the end of the above-described first DVS cycle, the same sample was submitted to a second DVS cycle with a second sorption phase and a second desorption phase. The results are shown in FIG. 18. Both second sorption and desorption phases were identical to the first desorption phase curve obtained during the first DVS cycle. Indeed, as can be seen in FIG. 18, desorption phase and sorption phase overlap each other. The di-hydrated form of N-(3-(4-(3-(diisobutylamino)propyl)piperazin-1-yl)propyl)-1H-benzo[d]imidazol-2-amine, 1 eq sulphate salt of example 3, which was obtained beyond 80% RH at 25° C. during the first cycle, was thus stable and non hygroscopic.

BIOLOGY EXAMPLES

In Vitro APP Metabolism Assay

This assay was performed using SH-5Y5Y cells (human neuroblastoma cell line overexpressing wild type human APP) which were treated for 24 h with the sulphate salt of example 2. This test was carried out at four different compound concentrations of 0.3, 1, 3 and 10 µM. Quantification of different metabolites was achieved by westernblot analysis. CTFα, CTFβ and AICD were analysed using anti-actin ((I-19) (SC-1616 Santa Cruz Biotechnology; 1:1000 from 200 µg/ml stock) as an internal control and anti-C term APP antibody (1:250000 in washing buffer). Protein concentrations were determined by the BCA Protein Assay Kit (Thermo Scientific). Samples (20 µg total protein) were separated by 16% SDS-PAGE according to the molecular weight of each protein, and transferred to nitrocellulose membranes.

The results are shown on FIGS. 19-*a*, 19-*b*, 19-*c* and 19-*d*. They show dose dependent increased levels of AICD, CTFα and sAPPα and decreased level of $A\beta_{1-42}$.

Sulphate salt of example 2 thus induces a significant increase of APP metabolism through non-amyloidogenic pathway concomitant with a reduction in the formation of deleterious metabolites involved in amyloid plaques formation. These results are all the more so remarkable since $A\beta_{1-42}$ is one of the most deleterious APP metabolism by-products with respect to amyloid plaques formation. Furthermore, peptide sAPPα does not induce amyloid plaque formation and is rather recognized as having beneficial neuroprotective effects.

In addition, it is remarked that no cytotoxicity was found for this sulphate salt, its $CC_{50}$ on SH-5Y5Y cell line was found greater than 30 µM. $CC_{50}$ is defined herein as the concentration at which 50% of plated cells remain alive.

In Vivo APP Metabolism Assay

In vivo experiments were carried out on 4-month old C57Bl6 female mice or 2-month old Sprague Dawley rats.

Acute Treatment: 24 h p.o.

C57Bl6 female mice were treated per os (gavage) with vehicle or compound (example 2) at 0.25, 0.5, 1, 3 and 6 mg/kg mg/kg (n=6 per group) for 24 h. The product was administered with a disposable Rodent Feeding Tube ECIMED Ref #V0104030 (4 mm×30 mm). The animals were sacrificed after 24 h, the brain was immediately removed for dissection. Levels of CTFα in the frontal cortex (FC) and/or the hippocampus (HIP) were measured by western-blot analysis as previously described. Briefly, tissues were homogenized with 200⍊ of lysis buffer (10 mL of Laemmli Pre-Lysis Buffer and 1 tablet of Protease Inhibitor cocktail Complete Mini (Roche)) in a potter. After sonication (5 min), homogenates were centrifuged at 1600 rpm 5 min 4° C. Supernatants were aliquoted and stored at −80° C. before western blot analysis.

Dose dependent results are shown on FIG. 20. Compound of example 2 enhances APP metabolism through the non-amyloidogenic pathway in the frontal cortex as shown by increasing concentrations of CTFα. The frontal cortex is generally the first region of the brain to be affected by amyloid plaques formation in abnormal APP metabolism related diseases.

The compound of example 2 was also compared to the oxalate salt of WO2006/051489 in the same assay (6 mg/kg dose). The results shown in FIG. 21 indicate superior efficiency of the sulphate salt in comparison to the oxalate salt.

Chronic Treatment: 1-Month

Rats were provided for one month with 1 or 10 mg/kg/day of the compound of example 2 dissolved in their drinking water. The remarkable high solubility of this sulphate salt enabled easy formulation and administration thereof to the animals. The animals were sacrificed after one month and levels of CTFα and CTFβ in the frontal cortex (FC) and/or the hippocampus (HIP) were measured by western-blot analysis as previously described. Dose dependent results are shown on FIGS. 22-a and 22-b. Sulphate salt of example 2 enhances APP metabolism through the non-amyloidogenic pathway in the frontal cortex as shown by increasing concentrations of CTFα (FIG. 22-a). Sulphate salt of example 2 attenuates APP metabolism through the amyloidogenic pathway in the hippocampus as shown by decreasing concentrations of CTFβ (FIG. 22-b). The frontal cortex is generally the first region of the brain to be affected by amyloid plaques formation in abnormal APP metabolism related diseases while the hippocampus, which is highly involved in memory and recollection processes, is latterly but severely affected. The sulphate salt of example 2 thus has very positive effect on APP metabolism in both the frontal cortex and the hippocampus and could is therefore of interest in the treatment of neurodegenerative diseases, in particular for both early and advanced stages of abnormal APP metabolism related diseases.

Chronic Treatment: 3-Months

Neuropathological disorders are also characterized by abnormal phosphorylation of Tau protein (AT100). Hyperphosphorylation of the tau protein (on specific sites) can result in the intracellular accumulation of neurofibrillary tangles (NFTs), involved in the pathogenesis of Alzheimer's disease and other tauopathies. One axis of the study was thus to study the effect of the sulphate salt of example 2 on this abnormal phosphorylation. In parallel, such effect was also monitored with regards to the non-pathological phosphorylation of Tau protein (AT8) which should remain unaffected. Another axis of this study was thus the impact of the sulphate salt of example 2 on oxidative stress (OS). Therefore, levels of lipidic peroxidation, a well known marker for the evaluation of oxidative stress, were determined. Indeed, oxidative stress (OS), by the generation of toxic reactive oxygen species (ROS) and oxidative damage (oxidation of vital cellular components as lipids, proteins and DNA), is believed to be involved in the pathogenesis of neurodegenerative disorders. The neuronal cell OS response is particularly studied for its contribution to the neurodegeneration processes. OS results from a misbalance between ROS generation and antioxidant defences, leading to an accumulation of oxidative damages, and finally the cell death. Oxidative damage has also been associated with pathological neuronal loss in Parkinson's disease (PD) and Huntington's disease (HD).

4-month old C57B16 female mice were provided with 0.5, 1 or 3 mg/kg of compound of example 2 dissolved in their drinking water. First of all, all mice were weighed and distributed in each cage in order to have approximately the same mean of weight±SD per cage. Each product concentration was prepared in sterile bottles and kept at RT protected from light. Drinking bottles were filled each week and weighed. Volume consumed was calculated by weighing each bottle after each week and the remaining volume was discarded.

AT100 phosphorylation levels measurements were performed on brain tissues by western blot analysis (previously described) using specific anti AT100 antibody (Anti-human PHF-Tau monoclonal antibody, MN1020, ThermoScientific/Pierce).

AT8 phosphorylation levels measurements were performed on brain tissues by western blot analysis (previously described) using specific anti AT8 antibody (Anti-human PHF-Tau monoclonal antibody, MN1060, ThermoScientific/Pierce).

LPO levels measurements: the level of lipid peroxidation in hippocampi is determined as cumene hydroperoxide (CHP) equivalents and expressed as CHP equivalents per wet weight of tissue and as percentage of control group data following the modified FOX assay.

The results are shown in FIGS. 23-a, 23-b and 23-c. The sulphate salt of the invention decreases the pathological Tau protein phosphorylation (FIG. 23-a) while not affecting the normal Tau protein phosphorylation (FIG. 23-b). Furthermore, this sulphate salt induces a significant decrease of LPO levels and is thus able to partly alleviate oxidative stress processes (FIG. 23-c).

In view of the above experimental results, sulphate salts of the invention are useful in orienting APP metabolism towards non-amyloidogenic pathways in the frontal cortex and the hippocampus. They further alter the pathological Tau protein phosphorylation while alleviating oxidative stress processes.

The invention claimed is:

1. A sulphate salt of N-(3-(4-(3-(diisobutylamino)propyl)piperazin-1-yl)propyl)-1H-benzo[d]imidazol-2-amine and pharmaceutically acceptable solvates thereof.

2. The sulphate salt of claim 1, having Formula II

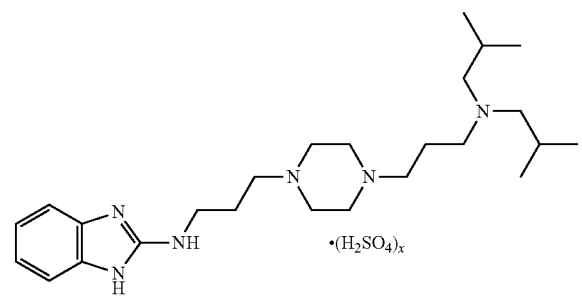

Formula II wherein x designates the number of equivalents of sulphuric acid and x is 0.5 to 4, and pharmaceutically acceptable solvates thereof.

3. The sulphate salt of claim 2 and pharmaceutically acceptable solvates thereof, wherein x is 1.5 to 2.5.

4. The sulphate salt of claim 2 and pharmaceutically acceptable solvates thereof, wherein x is 0.5 to 1.5.

5. The sulphate salt of claim 2 and pharmaceutically acceptable solvates thereof, wherein x is 2.5 to 3.5.

6. The sulphate salt of claim 2, having formula Formula III
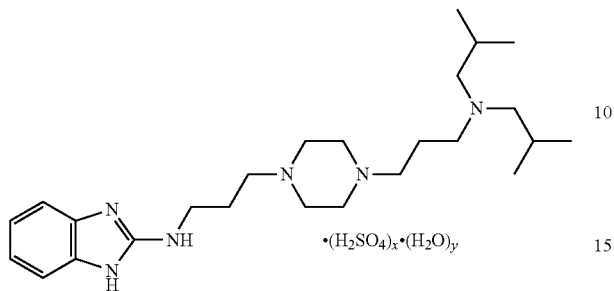
Formula III
wherein
x is as defined in claim 2, and
y designates the number of equivalents of water and y is 0.5 to 5.
7. A medicament comprising a sulphate salt according to claim 1, or a pharmaceutically acceptable solvate thereof.
* * * * *